(12) United States Patent
Pugh et al.

(10) Patent No.: US 7,544,480 B2
(45) Date of Patent: Jun. 9, 2009

(54) ASSAYS FOR MODULATORS OF ASPARAGINYL HYDROXYLASE

(75) Inventors: Christopher William Pugh, Oxford (GB); Jonathan Mark Gleadle, Oxford (GB); Peter John Ratcliffe, Oxford (GB); Christopher Joseph Schofield, Oxford (GB); Luke Alexander McNeill, Oxford (GB)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 10/515,419

(22) PCT Filed: May 23, 2003

(86) PCT No.: PCT/GB03/02257

§ 371 (c)(1),
(2), (4) Date: Jul. 15, 2005

(87) PCT Pub. No.: WO03/100438

PCT Pub. Date: Dec. 4, 2003

(65) Prior Publication Data

US 2005/0244915 A1 Nov. 3, 2005

(30) Foreign Application Priority Data

May 23, 2002 (GB) .................................. 0211920.4

(51) Int. Cl.
*C12Q 1/26* (2006.01)
(52) U.S. Cl. ....................................................... 435/25
(58) Field of Classification Search .................. None
See application file for complete search history.

(56) References Cited

U.S. PATENT DOCUMENTS

2006/0040265 A1\* 2/2006 Flamme et al. ................. 435/6

FOREIGN PATENT DOCUMENTS

WO WO 00/74725 A1 12/2000
WO WO 03/025013 A1 3/2003

OTHER PUBLICATIONS

Lando et al. Asparagine Hydroxylation of the HIF Transactivation Domain: A Hypoxic Switch; Science, vol. 295 (2002) pp. 858-861.\*
Seffernick et al. Melamine Deaminase and Atrazine Chlorohydrolase: 98 Percent Identical but Functionally Different; Journal of Bacteriology, vol. 183, No. 8 (2001) pp. 2405-2410.\*
Wells, J.A. Additivity of Mutational Effects in Proteins; Biochemistry, vol. 29, No. 37 (1990) pp. 8509-8517.\*
Lando, D. et al., "Asparagine Hydroxylation of HIF Transactivation Domain: A Hypoxic Switch", Science, Vo. 295, No. 5556, pp. 858-861, (Feb. 1, 2002).
Lando, D. et al., "FIH-1 is an Asparaginyl Hydroxylase Enzyme that Regulates the Transcriptional Activity of Hpoxia-Inducible Factor", Genes & Development, vol. 16, No. 12, pp. 1466-1471, (Jun. 15, 2002).
Hewitson, K. S. et al., "Hypoxia-Inducible Factor (HIF) Asparagine Hydroxylase is Identical to Factor Inhibiting HIF (FIH) and is Related to the Cupin Structural Family" The Journal of Biological Chemistry, vol. 27, No. 29, pp. 26351-26355, (Jul. 19, 2002).
McNeill, L. A. et al., "Hypoxia-Inducible Factor Asparaginyl Hydroxylase (FIH-1) Catalyses Hydroxylation at the β-Carbon of Asparagine-803", Biochemical Journal, Vo. 367, No. 3, pp. 571-575, (2002).
Mahon, P. C. et al., "FIH-1: A Novel Protein that Interacts with HIF-1α and VHL to Mediate Repression of HIF-1 Transcriptional Activity".
Freedman, S. et al., "Structural Basis for Recruitment of CBP/p300 by Hypoxia-Inducible Factor-1α", Proc. Natl. Acad. Sci. USA, vol. 99(8), Apr. 2002, pp. 5367-5372.
U.K. Patent Office Search Report for Application No. GB 0211920.4.
Lando, D. et al., "Asparagine Hydroxylation of HIF Transactivation Domain: A Hypoxic Switch", Science, Vo. 295, No. 5556, pp. 858-861, (Feb. 1, 2002).
Lando, D. et al., "FIH-1 is an Asparaginyl Hydroxylase Enzyme that Regulates the Transcriptional Activity of Hpoxia-Inducible Factor", Genes & Development, vol. 16, No. 12, pp. 1466-1471, (Jun. 15, 2002).
Hewitson, K. S. et al., "Hypoxia-Inducible Factor (HIF) Asparagine Hydroxylase is Identical to Factor Inhibiting HIF (FIH) and is Related to the Cupin Structural Family", The Journal of Biological Chemistry, vol. 27, No. 29, pp. 26351-26355, (Jul. 19, 2002).
McNeill, L. A. et al., "Hypoxia-Inducible Factor Asparaginyl Hydroxylase (FIH-1) Catalyses Hydroxylation at the β-Carbon of Asparagine-803", Biochemical Journal, Vo. 367, No. 3, pp. 571-575, (2002).
Mahon, P. C. et al., "FIH-1: A Novel Protein that Interacts with HIF-1α and VHL to Mediate Repression of HIF-1 Transcriptional Activity", (2001).
Freedman, S. et al., "Structural Basis for Recruitment of CBP/p300 by Hypoxia-Inducible Factor-1α", Proc. Natl. Acad. Sci. USA, vol. 99(8), Apr. 2002, pp. 5367-5372.
U.K. Patent Office Search Report for Application No. GB 0211920.4, (Dec. 14, 2000).

\* cited by examiner

*Primary Examiner*—Jon P Weber
*Assistant Examiner*—Paul C. Martin
(74) *Attorney, Agent, or Firm*—Wilmer Cutler Pickering Hale and Dorr LLP

(57) ABSTRACT

A method of identifying an agent which modulates hydroxylation of hypoxia inducible factor (HIF), comprises contacting a HIF asparagine hydroxylase and a test substance in the presence of a substrate of the hydroxylase under conditions in which asparagine in the substrate is hydroxylated in the absence of the test substance; and determining hydroxylation of the substrate. Preferably the substrate is a HIF polypeptide comprising HIF-1α, a fragment thereof comprising Asn 803 of HIF-1α or a peptide analogue of HIF-1α or fragment thereof comprising an asparagine equivalent to Asn 803 of HIF-1α and wherein hydroxylation of Asn 803 or of a said equivalent asparagine is determined.

16 Claims, 4 Drawing Sheets

|  | HIF-1α 775-826 |  |  | HIF-1α 775-826 N803A |  |
|---|---|---|---|---|---|
| N-oxaloylglycine | − | − | + | − | − |
| FIH | − | + | + | − | + |

← Gal-CH1

FIGURE 1b

```
          -{||||||||||||||||||||||||||-                                          1                                              2
CAS1      TMEAMLGLVGRRLGLHTG- - - - - - - - - - - -YRELRSGTVYHDVYP-SPGAHHLSSETSETLLEFHTEMAYH
FIH1      -NDTVGGKIVMDFLGFNWNWINKQQGKRGWGQLTSNLLLIGMEGN- - - - - - - - - - - - -VTPAHYDEQQN
PHD3      AISFLLSLIDR-LVLYCGSRLGKY- - - - -YVKERSKAMVACYPGNG- - - - - - - - - - -TGYVRHVDNPN-
PMI       NNQTLRDLVTAKPQEYLGESIITK- - - - -FGSSKELPFLFKVLSIE- - - - - - - - - - - -KVLSIQAHP-[16]
                                                                                            ▲▲

3                     4
CAS1      RLQPNYVMLACSRADHERTAATLVASVRKAUPLLDERTRARLLDRRMPCCVDVAFRGGVDDPGAIAQVKP
FIH1      FFAQIKGYKRC- - - - - - - - - -ILFPP- -DQFECL-YPYP- - - - -VHHPC- -DRQSQVDFDNPD- - - - - - -
PHD3      - - - - - -GDGRC- - - - - - - - - - - - - - - - - - - -HTCIYYLNKNW- - - - - - - - -DAKLHGGI- - - - - - - - - - - - -
PMI       - - -PEMAIAVTDFEGF- - -CGFKPLDQLAKTLATVPELNEIIGQELVDEFISGIKLPAEVG- - - -(40)- - - -

5              6           7
CAS1      LYGDADDPFLGYDRELLAPEDPADKEAVAALSKALD-EVTEAVYLEPGDLIV-DNFRTTHART- -PFSP
FIH1      - - - - - - - - - - -YER-F- - - -PNFQNVV- - - - - - - -GYETVV-GPGDVLYI-PMY-WWHIESL- - - -
PHD3      - - - - - - - - - - - - - -LRIF- - - -PEGKSFIADVEPIF- - - - - - - - -DRLLFFWSDRRNPHEVQ- - - - - -
PMI       - - - - -PQVFKDIDSRLPELIQRLNKQFRNDIGLFCGCLLLNHVGLNKGEAMFL- -QAKDPHAYI- - - - - - -
                                                                                         ▲

8
CAS1      RWDGKDR- WL- - - -HRVYPRTDR- - - - -NGQLSGGERAGDVVAFTPRG-
FIH1      -LNGGIT- ITVNFWYKGAPTPKRIEYPLKAHQKVAIMRNIEKMLGEALGN
PHD3      -PSYATRYAMTVWY- -FDAEERAE- - -AKKKFRNLTRKTESALTED- - - -
PMI       - -SGOIIECM- - - - - - -AASDNVV- - - - -RAGFTPKFKDVKNLVEML- - -
              ▲
```

FIGURE 2a

ASSAYS FOR MODULATORS OF ASPARAGINYL HYDROXYLASE

This is a national stage application of International Application No. PCT/GB03/02257, filed May 23, 2003, which claims benefit of priority to GB 0211920.4, filed May 23, 2002.

FIELD OF THE INVENTION

The invention relates to hydroxylases which act on hypoxia inducible factor (HIF) and which are involved in activation of HIF related activity. The invention also relates to modulators of such hydroxylases and their use in methods of treatment.

BACKGROUND OF THE INVENTION

Hypoxia in animals activates a broad range of homeostatic responses via induction of a transcriptional complex termed hypoxia inducible factor (HIF). HIF is a heterodimer of $\alpha$- and $\beta$-subunits, with regulation by dioxygen availability being mediated by post-translational modification of the $\alpha$-subunits. In mammalian cells, at least two HIF-$\alpha$ subunit isoforms (HIF-1$\alpha$ and HIF-2$\alpha$) are regulated by dioxygen levels. Each HIF-$\alpha$ protein contains an internal oxygen dependent degradation domain (ODDD) possessing targeting motifs for proteolytic regulation and a C-terminal transactivation domain (CAD) independently regulated by dioxygen, irrespective of changes in protein abundance, through interaction with the CH1 domain of the co-activator p300.

The oxygen dependent degradation of HIF-$\alpha$ by proteolysis is regulated by the hydroxylation of specific prolyl residues (Pro-402 and Pro-564 in human HIF-1$\alpha$) that mediate recognition of HIF-$\alpha$ by the von Hippel-Lindau (VHL) ubiquitinylation complex, and consequent proteasomal destruction. Combined structural analysis and genetic approaches led to the identification of three isoforms of human HIF prolyl hydroxylase (PHD1-3, prolyl hydroxylase domain) together with homologues in a range of organisms. In vitro analyses, together with sequence and mutational analyses identified these as belonging to a sub-family of the Fe(II) and 2-oxoglutarate (2-OG) dependent oxygenases. Limiting oxygen availability in hypoxia, or direct inhibition of the PHD enzymes by cobaltous ions and iron chelators, allows HIF-$\alpha$ to escape hydroxylation and recognition by pVHL, providing insights into the mechanism by which these stimuli suppress HIF-$\alpha$degradation and activate the transcriptional cascade.

Previous analyses of the HIF-$\alpha$ CAD have indicated that, as with proteolysis, the action of hypoxia is mimicked by cobaltous ions and iron chelators.

Mass spectrometric and mutational analyses of the HIF-$\alpha$ CAD demonstrate regulatory hydroxylation of a specific asparaginyl residue (Asn-803 in HIF-1$\alpha$). In the presence of oxygen, hydroxylation at this site prevents interaction with the p300 CH1 domain, whereas in hypoxia suppression of the modification allows interaction with p300 and transcriptional activation. Consistent with this model, NMR studies of the human HIF-1$\alpha$ CAD complexed to CH1 indicate that the unmodified Asn-803 is buried at the interface between the proteins.

SUMMARY OF THE INVENTION

The present inventors have now identified that hydroxylation of Asn-803 in HIF-1$\alpha$ is catalysed by Factor Inhibiting HIF (FIH). Hydroxylation of Asn-803 interferes with interaction of p300 CH1 domain, and thus reduces transcriptional activation mediated by HIF.

In accordance with the present invention, there is provided an assay for identifying an agent which modulates asparagine hydroxylation of HIF, the method comprising:
    contacting a HIF asparagine hydroxylase and a test substance in the presence of a substrate of the hydroxylase under conditions which allow hydroxylation of the substrate in the absence of the test substance; and
    determining hydroxylation of the substrate.

The invention also relates to the use of substances identified in accordance with the assays of the present invention and to the use of modulators of the asparagine hydroxylases described herein in the treatment of a condition or disease associated with altered HIF levels with respect to healthy or normal levels, or a condition in which it is desired to alter HIF activity.

DESCRIPTION OF THE SEQUENCES

SEQ ID NO: 1 comprises the nucleotide and amino acid sequence for FIH, HIF asparagine hydroxylase.

SEQ ID NO: 2 comprises the amino-acid sequence for FIH.

SEQ ID NO: 3 comprises the amino acid sequence of a modified FIH.

SEQ ID NOs: 4 to 13 are primers used in the Examples.

DETAILED DESCRIPTION OF THE INVENTION

The present invention relates to identification of HIF asparagine hydroxylase and provides for the use of such hydroxylases in assay methods to identify modulators of HIF mediated activity.

In preferred aspects of the invention, a HIF hydroxylase, variant or fragment for use in accordance with the invention has the ability to hydroxylate one or more residues of HIF-1$\alpha$, preferably asparaginyl residue of HIF and in particular Asn 803 of HIF-1$\alpha$ or a peptide analogue of HIF-1 or fragment thereof incorporating such an asparaginyl. Preferably, a variant of a HIF asparagine hydroxylase in accordance with the present invention has at least 60% sequence identity with the amino acid sequence of SEQ ID NO: 2, preferably greater than 70%, more preferably greater than about 80%, 90% or 95% sequence identity.

The present invention also includes use of active portions, fragments, derivatives and functional mimetics of the polypeptides of the invention. An "active portion" of a polypeptide means a peptide which is less than said full length polypeptide, but which retains hydroxylase activity and in particular maintains HIF asparagine hydroxylase activity. Such an active fragment may be included as part of a fusion protein, e.g. including a binding portion for a different i.e. heterologous ligand.

Typically, polypeptides with more than about 60% identity preferably at least 70%, at least 80% or at least 90% and particularly preferably at least 95% or at least 99% identity, with the amino acid sequence of SEQ ID NO: 2, are considered as variants of the proteins. Such variants may include allelic variants and the deletion, modification or addition of single amino acids or groups of amino acids within the protein sequence, as long as the peptide retains asparagine hydroxylase activity. Preferably a variant of SEQ ID NO: 2 will have the same domain structure as FIH, i.e. an eight strand $\beta$ barrel jelly roll.

Amino acid substitutions may be made, for example from 1, 2 or 3 to 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling (molecular breeding) techniques.

Shorter polypeptide sequences are within the scope of the invention. For example, a peptide fragment of at least 20 amino acids or up to 50, 60, 70, 80, 100, 150 or 200 amino acids in length is considered to fall within the scope of the invention. In particular, but not exclusively, this aspect of the invention encompasses the situation when the protein is a fragment of the complete protein sequence and may represent a catalytic region, capable of hydroxylating Asn 803 of HIF-α. Such fragments can be used to construct chimeric molecules.

Polypeptides of the invention may be chemically modified, e.g. post-translationally modified. For example, they may be glycosylated or comprise modified amino acid residues. They may also be modified by the addition of histidine residues to assist their purification or by the addition of a nuclear localisation sequence to promote translocation to the nucleus or by post translational modification including hydroxylation or phosphorylation. Such modified polypeptides fall within the scope of the term "polypeptide" of the invention.

The polypeptides of the invention may be used in assays for asparaginyl hydroxylase activity on substrates such as HIF. The polypeptides may also be used for hydroxylation of suitable substrates and in particular asparaginyl hydroxylation of such substrates, in particular where it is desired to have specific hydroxylation of asparagine with little or no hydroxylation of other residues such as aspartic acid. A variant or an active fragment of a HIF asparagine hydroxylase of the invention may typically be identified by monitoring for hydroxylase activity as described in more detail below.

Such HIF asparagine hydroxylases may be a eukaryotic polypeptide, preferably a mammalian polypeptide, more preferably a human polypeptide such as that of SEQ ID NO: 2.

A HIF asparagine hydroxylase preferably contains a jelly roll (double stranded beta helix/β barrel jelly roll) structure consisting of a minimum of eight strands. Typically, the jelly roll structure may have eight strands, although an insert is preferably present between β strands 4 and 5 of the jelly roll. Preferred HIF hydroxylases contain the sequence;

HXD/E[X]$_n$H where X is any amino acid and n is between 1 and 200, 20 and 150 or 30 and 100 amino acids, for example 10, 20, 30, 40, 50, 60, 70, 80, 90 or 100 amino acids.

Nucleotides according to the invention encoding HIF asparaginyl hydroxylase have utility in production of the proteins according to the invention, which may take place in vitro, in vivo or ex vivo. The nucleotides may be involved in recombinant protein synthesis or indeed as therapeutic agents in their own right, utilised in gene therapy techniques. Nucleotides complementary to those encoding HIF asparagine hydroxylase, or antisense sequences, or interfering RNA may also be used in gene therapy.

A polynucleotide of the invention can hybridize to the coding sequence or the complement of the coding sequence of SEQ ID NO: 1 at a level significantly above background. Background hybridization may occur, for example, because of other cDNAs present in a cDNA library. The signal level generated by the interaction between a polynucleotide of the invention and the coding sequence or complement of the coding sequence of SEQ ID NO: 1 is typically at least 10 fold, preferably at least 100 fold, as intense as interactions between other polynucleotides and the coding sequence of SEQ ID NO: 1. The intensity of interaction may be measured, for example, by radiolabelling the probe, e.g. with $^{32}$P Selective hybridisation may typically be achieved using conditions of medium to high stringency. However, such hybridisation may be carried out under any suitable conditions known in the art (see Sambrook et al, 1989. For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 1 may be modified by nucleotide substitutions, for example from 1, 2 or 3 to 10, 25, 50 or 100 substitutions. The polynucleotide of SEQ ID NO: 1 may alternatively or additionally be modified by one or more insertions and/or deletions and/or by an extension at either or both ends. A polynucleotide may include one or more introns, for example may comprise genomic DNA. The modified polynucleotide generally encodes a polypeptide which has asparagine hydroxylase activity. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 1 will generally have at least 50%, at least 57%, at least 60%, at least 70%, at least 80%, at least 88%, at least 90%, at least 95%, at least 98% or at least 99% sequence identity to the coding sequence of SEQ ID NO: 1 over a region of at least 20, preferably at least 30, for instance at least 40, at least 60, more preferably at least 100 contiguous nucleotides or most preferably over the full length of SEQ ID NO: 1. Preferably the nucleotide sequence encodes a polypeptide which has the same domain structure as FIH.

For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al (1990) J. Mol. Biol. 215:403-10.

Software for performing BLAST analyses is publicly available through the National Centre for Biotechnology Information (www.ncbi.nlm.mh.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787 and Altschul and Gish (1996) *Methods Enzymol.* 266: 460-480. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

The present invention also includes expression vectors that comprise nucleotide sequences encoding the proteins of the invention. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. 1989.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used as test compounds in the assays of the invention or may be useful in a method of treatment of the human or animal body by therapy.

Polynucleotides of the invention may also be used to design double stranded RNAs for use in RNA interference. Such RNA comprises short stretches of double stranded RNA having the same sequence as a target mRNA. Such sequences can be used to inhibit translation of the mRNA. Alternatively, small fragments of the gene encoding a HIF asparagine hydroxylase may be provided, cloned back to back in a plasmid. Expression leads to production of the desired double stranded RNA. Such short interfering RNA (siRNA) may be used for example to reduce or inhibit expression of a HIF hydroxylase of the invention, in assays or in a method of therapy. The invention also relates to such siRNAs. Such siRNAs may be designed to inhibit groups of HIF hydroxylases of the invention by basing their sequences on regions of conserved sequence in the encoding genes of the hydroxylases. Alternatively, the siRNAs may be made specific to a particular HIF hydroxylase by choosing a sequence unique to the encoding gene of the particular hydroxylase gene to be inhibited.

Preferably, a polynucleotide of the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vector may be an artificial chromosome. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example in a method of gene therapy.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. An IRES promoter may also be used. All these promoters are readily available in the art.

Mammalian promoters, such as β-actin promoters, may be used. Tissue-specific promoters are especially preferred. Inducible promoters are also preferred. Promoters inducible by hypoxic conditions may, for example, be employed. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or HPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Homologous recombination may also be used to disrupt or mutate endogenous sequences in cells encoding HIF asparagine hydroxylases. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

The invention also includes cells that have been modified to express a HIF asparagine hydroxylase of the invention.

Assays

Our data shows that hydroxylation of HIF-α CAD is mediated by an asparagine hydroxylase enzyme. The enzyme responsible is referred to as HIF asparagine hydroxylase and includes FIH. The action of HIF asparagine hydroxylases, and in particular human HIF hydroxylases, represent a novel target for the control of HIFα. By blocking HIF asparagine hydroxylase activity, this will reduce hydroxylation of HIF-α and thus lead to an increase in the interaction with p300 and in particular the CH1 domain and thus transcriptional activation. This in turn will lead to the activation of systemic local defences against hypoxia or ischaemia that may include the promotion of angiogenesis, erythropoiesis, energy metabolism, inflammation, vasomotor function, and will also affect apoptotic/proliferative responses.

We describe below in more detail a number of different assays that may be carried out to identify modulators of HIF hydroxylase activity and in particular of asparagine hydroxylase activity, or which affect regulation of HIF-α interaction with p300 in a cell and hence which affect HIF mediated activity. Some of these assays utilise HIF polypeptides, and in particular HIF asparagine hydroxylases in accordance with the present invention. Typically, the assays may utilise a human HIF asparagine hydroxylase such as FIH or a fragment or variant of a human HIF asparagine hydroxylase. Non-human HIF hydroxylases may also be used. These components are described in more detail below. Each of these components, where required may be provided either in purified or unpurified form, for example, as cellular extracts or by purification of the relevant component from such extracts. Alternatively, the relevant component can be expressed using recombinant expression techniques and purified for use in the assay. Alternatively, the components may be expressed recombinantly in a cell for use in cell based assays.

Typically, a polynucleotide encoding the relevant component is provided within an expression vector. Such expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art, such as those described in more detail herein with reference to the HIF hydroxylases. Promoter sequences may be inducible or constitutive promoters depending on the selected assay format. The promoter may be tissue specific. Examples of promoters and other flanking sequences for use in the expression vectors are described in more detail herein with reference to the HIF hydroxylases of the invention and in particular to the human HIF hydroxylases of the invention.

HIF Polypeptides and Peptide Analogues

The assays of the present invention may use a substrate of a HIF asparagine hydroxylase and in particular an asparagine containing substrate of the enzyme. In particular, such substrates may be used in assays to monitor for the activity of a modulator of HIF asparagine hydroxylase activity. The substrate may be a HIF polypeptide or peptide analogue thereof. Typically, a HIF polypeptide will be used as the substrate.

Any suitable substrate in which an asparagine residue is hydroxylated by a HIF hydroxylase of SEQ ID NO: 2 may be used. In preferred embodiments: of the invention, such a substrate is a HIF polypeptide such as a HIF-1α or HIF-2α subunit protein or fragment of either or peptide analogue of the subunit or fragment. Preferably, the HIF-α peptide conveys an oxygen regulated response. Preferably, the HIF-α peptide has a CAD domain and is capable of oxygen regulated interaction with p300 and downstream transcriptional activation. Preferably, such HIF-αpeptides are capable of interacting with the p300 CH1 domain. Preferably, such HIF polypeptides, fragments or peptide analogues incorporate an asparagine residue equivalent to Asn 803 defined with reference to HIF-1α. The asparagine equivalent to Asn 803 of HIF-1α may be determined by aligning the HIF variant, fragment or analogue to the sequence of HIF-1α to obtain the best sequence alignment and identifying thereby the asparagine equivalent to Asn 803 of HIF-1α. A HIF polypeptide may be of eukaryotic origin, in particular a human or other mammalian, HIF-α subunit protein or fragment thereof. Alternatively, the polypeptide may be of *C. elegans* origin. In those assays which monitor for hydroxylation of HIF-α through its interaction with p300, the HIF polypeptide has the ability to bind to a wild type full length p300 protein or a fragment thereof comprising the CH1 domain. Preferably, such binding is able, in a hypoxic cellular environment, to activate transcription.

A number of HIFα subunit proteins have been cloned. These include HIF-1α, the sequence of which is available as Genbank accession number U22431, HIF-2α, available as Genbank accession number U81984 and HIF-3α, available as Genbank accession numbers AC007193 and AC079154. These are all human HIF α subunit proteins and all may be used in the invention. HIF-α subunit proteins from other species, including murine HIF-1α (accession numbers AF003695, U59496 and X95580), rat HIF-1α (accession number Y09507), murine HIF-2α (accession numbers U81983 and D89787) and murine HIF-3α (accession number AF060194) may also be used in the invention.

One HIF-α protein of particular interest is the *C. elegans* HIF-α subunit protein. The *C. elegans* system may be used in assays of the present invention.

There are a number of common structural features found in the two HIF-α subunit proteins identified to date. Some of these features are identified in O'Rourke et al (1999, J. Biol. Chem., 274; 2060-2071) and may be involved in the transactivation functions of the HIF-α subunit proteins. One or more of these common structural features are preferred features of the HIF polypeptides.

Variants of the above HIF-α subunits may be used, such as synthetic variants which have at least 45% amino acid identity to a naturally occurring HIF-α subunit (particularly to a human HIF-α subunit such as, for example HIF-1α), preferably at least 50%, 60%, 70%, 80%, 90%, 95% or 98% identity. Such variants may include substitutions or modifications as described above with respect to HIF hydroxylases. Amino acid activity may also be calculated as described above with reference to HIF hydroxylases.

HIF fragments may also include non-peptidyl functionalities and may be optimised for assay purposes such that the level of identity is lowered. Such functionalities may be covalently bound such as sugars or non-covalently bound such as metal ions.

HIFα polypeptides as described herein may be fragments of the HIF-α subunit protein or variants as described above, provided that said fragments retain the ability to interact with a wild-type p300 CH1 domain. When using proteinogenic amino acid residues, such fragments are desirably at least 20, preferably at least 40, 50, 75, 100, 200, 250 or 400 amino acids in size. Desirably, such fragments include asparagine 803.

Cell based assays of the present invention may involve upregulation of an endogenous HIF-α or expression of a HIF-α by recombinant techniques and in particular of HIF-1α.

Assay Methods

The present invention provides an assay method for identifying an agent which modulates asparagine hydroxylation of hypoxia inducible factor. The method comprises contacting a HIF asparagine hydroxylase and a test substance, such as a potential inhibitor, in the presence of a substrate of the hydroxylase under conditions in which asparagine hydroxylation occurs in the absence of the test substance and determining the extent of asparagine hydroxylation of the substrate. Alternatively, the assay may be used to detect substances that increase the activity of the HIF asparagine hydroxylase by assaying for increases in activity.

In the Experiments described herein, FIH has been found to hydroxylate HIF-α at an asparagine residue within the CAD domain. This hydroxylation mediates p300 binding and in particular, reduces p300 binding. Such binding leads to transcriptional activation. This interaction and activation may also be used as the basis for an assay of the invention.

Such assays of the present invention may be used to identify inhibitors of HIF asparagine hydroxylase activity and are thus preferably carried out under conditions under which asparagine hydroxylation would take place in the absence of the test substance. In the alternative, the assays may be used to look for promoters of asparagine hydroxylase activity, for example, by looking for increased hydroxylation of asparagine substrates compared to assays carried out in the absence of a test substance. The assays may also be carried out under conditions in which hydroxylation is reduced or absent, such as under hypoxic conditions and the presence of or increased hydroxylation could be monitored under such conditions. The assays of the invention may also be used to identify inhibitors or activitators which are specific for HIF asparagine hydroxylases and which do not have activity or are less active with other hydroxylases, for example, such as HIF prolyl hydroxylases or other asparagine/aspartamic acid hydroxylases.

The present invention also provides an assay method for the identification of other HIF asparagine hydroxylases. The method typically comprises providing a test polypeptide; bringing into contact a HIF polypeptide and the test polypeptide under conditions in which the HIF polypeptide is hydroxylated at an asparagine residue by HIF hydroxylase and determining whether or not the HIF polypeptide is hydroxylated at the asparagine residue.

Further, other proteins are clearly related to FIH by sequence including active site residues and specifically those residues that are involved in binding the asparagine residue that is hydroxylated in HIF. These include those represented by SWALL database codes: Q9NWJ5, Q8TB10, Q9Y4E2, O95712, Q9H8B1, Q9NWT6 in *Homo sapiens*, and Q91W88 and Q9ER15 in *Mus musculus* (FIH=Q969Q7). Some or all of these have already been associated with transcription (Clissold P M, Ponting C P, JmjC: cupin metalloenzyme-like domains in jumonji, hairless and phospholipase A(2)beta TRENDS BIOCHEM SCI 26 (1): 7-9 January 2001), thus specific modulation of FIH activity alone or the modulation of FIH activity together with at least one of the related enzymes is of interest.

The present invention also provides an assay method for identifying alternative substrates of the HIF asparagine hydroxylase of the invention. Such assay method typically comprises contacting a test polypeptide with a HIF asparagine hydroxylase of the invention under conditions in which HIF would normally be hydroxylated at asparagine by the hydroxylase and determining whether the test polypeptide is hydroxylated at asparagine.

Methods for Monitoring Modulation

The precise format of any of the screening or assay methods of the present invention may be varied by those of skill in the art using routine skill and knowledge. The skilled person is well aware of the need to additionally employ appropriate controlled experiments. The assays of the present invention may involve monitoring for asparagine hydroxylation of a suitable substrate, monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects such as binding of HIF by p300 and downstream effects mediated by HIF such as HIF mediated transcription using suitable reporter constructs or by monitoring for the upregulation of genes or alterations in the expression patterns of genes know to be regulated directly or indirectly by HIF.

Various methods for determining hydroxylation are known in the art and are described and exemplified herein. Any suitable method may be used for determining activity of the HIF hydroxylase such as by substrate or co-substrate utilization, product appearance such as peptide hydroxylation or down-stream effects mediated by hydroxylated or non-hydroxylated products.

Our finding that the Asn 803 residue of HIF-1α is hydroxylated by an asparagine hydroxylase provides the basis for assay methods designed to screen for inhibitors or promoters of this process. Any suitable method may be used to monitor for hydroxylation of HIF-1α or a HIF polypeptide or analogue thereof. Assays may be carried out to monitor directly for hydroxylation of the relevant asparagine residue or another position. Alternatively, assays may be carried out to monitor for depletion of co-factors and co-substrates. Alternatively, such assays may monitor the downstream effects of hydroxylation of HIF or indeed inhibition of hydroxylation of HIF, for example, by monitoring the interaction between HIF and p300 or HIF mediated transcription. Alternatively, reporter gene constructs driven by HIF regulated promoters may be used. Assays are also provided for the identification of enhancers of the activity of the HIF asparagine hydroxylase. Such enhancers may be used to reduce HIFα activity.

In one embodiment, a suitable substrate of the HIF asparagine hydroxylase is provided. This may be HIF-α or a fragment thereof which includes a CAD domain or which includes a residue equivalent to Asn 803 of HIF-1α. The substrate may not be initially hydroxylated at the Asn 803 position. This may be achieved by providing synthetic polypeptide substrates, or by producing HIF-α polypeptides in bacterial cells, insect cells or mammalian cells or in in vitro transcription and translation systems. Alternatively, assays may be carried out over a selected time course such that the substrate is produced during the course of the assay, initially in un-hydroxylated form.

The substrate, enzyme and potential inhibitor compound may be incubated together under conditions which, in the absence of inhibitor provide for hydroxylation of Asn 803, and the effect of the inhibitor may be determined by determining hydroxylation of the substrate. This may be accomplished by any suitable means. Small polypeptide substrates may be recovered and subject to physical analysis, such as mass spectrometry or chromatography, or to functional analysis, such as the ability to bind to p300 (or displace a reporter molecule from p300). Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

Inhibitor compounds which are identified in this manner may be recovered and formulated as pharmaceutical compositions.

Another assay of the invention is for a promoter of asparagine hydroxylation of HIF-α subunits. Typically, a HIF-α subunit or portion thereof is prepared as described above, and incubated under hypoxic conditions. By "hypoxic", it is meant less than 5%, preferably less than 3%, more preferably less than 1%, end preferably less than 0.5%, such as less than 0.1% $O_2$. The HIF-α subunit is incubated with a cell extract which includes the HIF asparagine hydroxylase as described above, optionally further in the presence of a source of ferrous (FeII) ions, and/or other co-factors. A suitable concentration of ferrous ions is in the range of from 1 to 500 µM, such as from 25 to 250 µM and in particular from 50-200 µM. Ferrous ions may be supplied in the form of ferrous chloride, ferrous sulphate, and the like.

In this embodiment of the invention, the substrate will be incubated in the presence of a potential hydroxylation promoting agent, and the effect of the agent determined, by determining the hydroxylation of the Asn 803. As with the assay of the other aspect of the invention described above, determination may be quantitative or qualitative, and in either case determined relative to a suitable control.

The interaction between HIF and p300 is mediated by hydroxylation of HIF. Assays in accordance with the present invention may involve monitoring for the interaction between p300 and HIF. In particular, the interaction can be monitored for example by the use of fluorescence polarisation, surface plasmon resonance or mass spectrometric analysis. In the first instance, the fluorescence polarisation of a dye attached to the test polypeptide changes when interaction with p300 occurs, an interaction which is itself dependent on the hydroxylation state of the test polypeptide. In the second instance, a test polypeptide may be immobilised on a chip constructed such that binding events may be detected by a change in force exerted on the chip. "Native" or "soft ionisation" mass spectrometry can be used as an assay for hydroxylase activity; thus interactions between HIFα polypeptide, or fragment thereof containing the C-terminal transactivation domain, and p300 are observed by mass spectrometry, whereas upon hydroxylation, this interaction may be reduced or abrogated. Transcription and expression of genes known to be upregulated or down regulated by the presence of HIF can be monitored. In particular, upregulation of HIF regulated genes would demonstrate inhibition of asparagine hydroxylation whereas down regulation would suggest enhancement or promotion of asparagine hydroxylation.

In alternative embodiments, reporter constructs may be provided in which promoters mediated by HIF are provided operably linked to a reporter gene. Any suitable reporter gene could be used, such as for example enzymes which may then be used in colorometric, fluorometric, fluorescence resonance or spectrometric assays.

HIF asparagine hydroxlase is a 2OG dependent oxygenase.

In the assay methods described herein, typically the HIF asparagine hydroxylase and the substrate of the hydroxylase are contacted in the presence of a co-substrate, such as 2-oxoglutarate (2OG) or dioxygen. The hydroxylase activity of the HIF hydroxylase may be determined by determining the turnover of the co-substrate. This may be achieved by determining the presence and/or amount of reaction products, such as hydroxylated substrate or succinic acid. The amount of product may be determined relative to the amount of substrate. Typically, in such embodiments the substrate may be an HIF-α polypeptide and, for example, the product measured may be hydroxylated HIF-α polypeptide. For example, the extent of hydroxylation may be determined by measuring the amount of hydroxylated HIFα polypeptide, succinate or carbon dioxide generated in the reaction, or by measuring the depletion of 2OG or dioxygen. Methods for monitoring each of these are known in the scientific literature.

HIFα asparagme hydroxylase activity may be determined by determining the turnover of said 2OG to succinate and $CO_2$, as described in Myllyhaiju J. et al EMBO J. 16 (6): 1173-1180 (1991) or as in Cunliffe C. J. et al Biochem. J. 240 617-619 (1986), or other suitable assays for $CO_2$, bicarbonate or succinate production.

Unused 2OG may be derivatised by chemical reagents, exemplified by but not limited to hydrazine derivatives and ortho-phenylene diamine derivatives, to give indicative chromophores or fluorophores that can be quantified and used to indicate the extent of hydroxylation of the test polypeptide. Dissolved oxygen electrodes, exemplified by but not limited to a "Clarke-type" electrode or an electrode that uses fluorescence quenching, may be used to follow the consumption of oxygen in an assay mixture, which can then be used to indicate the extent of hydroxylation of the test polypeptide in an analogous manner to the above.

Alternatively, the end-point determination may be based on conversion of HIFα or peptide fragments (including synthetic and recombinant peptides) derived from HIFα into detectable products. Peptides may be modified to facilitate the assays so that they can be rapidly carried out and may be suitable for high throughput screening.

For example, reverse phase HPLC (C-4 octadecylsilane column), as exemplified herein, may be used to separate starting synthetic peptide substrates for HIF hydroxylase from the asparagine hydroxylated products, as the latter have a shorter retention time in the column. Modifications of this assay or alternative assays for HIF hydroxylase activity may employ, for example, mass spectrometric, spectroscopic, and/or fluorescence techniques as are well known in the art (Masimirembwa C. et al Combinatorial Chemistry & High Throughput Screening (2001) 4 (3) 245-263, Owicki J. (2000) J. Biomol. Screen. 5 (5) 297-305, Gershkovich A et al (1996) J. Biochem. & Biophys. Meths. 33 (3) 135-162, Kraaft G. et al (1994) Meths. Enzymol. 241 70-86). Fluorescent techniques may employ versions of the substrate modified in such as way as to carry out or optimise spectroscopic or fluorescence assays.

For example, HIFα polypeptide may be immobilised e.g. on a bead or plate, and hydroxylation of the appropriate residue detected using an antibody or other binding molecule which binds the CAD binding domain of HIFα with a different affinity when an asparagine 803 is hydroxylated from when the residue is not hydroxylated. Such antibodies may be obtained by means of standard techniques which are well known in the art, e.g. using a hydroxylated HIFα peptide.

Binding of a molecule which discriminates between the hydroxylated and non-hydroxylated form of a HIFα polypeptide may be assessed using any technique available to those skilled in the art, which may involve determination of the presence of a suitable label.

Assay methods of the present invention may also take the form of an in vivo assay. The in vivo assay may be performed in a cell line such as a yeast strain in which the relevant polypeptides or peptides are expressed from one or more vectors introduced into the cell.

In Vivo Assays

The assays may be carried out using cell based, organ based or whole animal assays conducted in vivo. Such assays may utilize the endogenous expression of the HIF hydroxylase nucleotides and/or polypeptides. In other forms of the invention, upregulation of specific endogenous HIF hydroxylases may be achieved by stimulators of the expression thereof. Such stimulators may be growth factors or chemicals that upregulate specific HIF asparagine hydroxylases. In another form of the invention, nucleotide constructs may be introduced into cells or transgenic animals to increase production of one or more specific HIF asparagine hydroxylases. Alternatively nucleotide constructs may be introduced into cells so as reduce or abrogate expression of one or more specific HIF hydroxylases. Appropriate methods that include but are not limited to homologous recombination, antisense expression, ribozyme expression and RNA interference are outlined herein and known by those skilled in the art.

Tissue culture cells, organs, animals and other biological systems, obtained by the aforementioned forms of the invention, may be used to provide a further source of a HIF hydroxylase, or may be used for the assay, or especially comparative assay, of the activity of test substances may inhibit, augment, block or otherwise modulate the activity of specific HIF hydroxylases.

The activity of the HIF hydroxylases may be assayed by any of the aforementioned methods or by cell, tissue, or other assays conducted in vivo that measure the effects of altered activity of the HIF hydroxylases.

HIF complexed with p300 activate hypoxia response elements that are found in the promoters and/or enhancers of endogenous genes that are regulated by the said HIF complexes. Such hypoxia response elements may also be isolated and operationally linked to reporter genes so as to assay the activity of the HIF complex through detection and/or quantitation of the reporter gene or its product. Therefore in a further form of the invention the activity of a HIF-α polypeptide that is regulated by HIF asparagine hydroxylase will be assayed by measuring the effects of the HIF complex on the expression of an endogenous gene or reporter gene that is functionally linked to a HIF binding hypoxia response element. Examples of endogenous genes that are regulated in this way are to be found in the role of the aryl hydrocarbon nuclear translocator (ARNT) in hypoxic induction of gene expression, see for example, Studies in ARNT-deficient cells. S. M. Wood, J. M. Gleadle, C. W. Pugh, O. Hankinson, P. J. Ratcliffe. Journal of Biological Chemistry 271 (1996) 15117-15123, and Hypoxia inducible expression of tumor-associated carbonic anyhydrases, C. C. Wykoff, N. J. P. Beasley, K. J. Turner, J. Pastorek, A. Sibtain. G. D. Wilson, H. Turley, K. Talks, P. H. Maxwell, C. W. Pugh, P. J. Ratcliffe, A. L. Harris. Cancer Research 60 (2000) 7075-7083. Examples include but are not limited to glucose transporter isoform 1, phosphoglycerate kinase-1, carbon anhydrase isoform 9, vascular endothelial growth factor. Each of said genes contains one or hypoxia response elements that may be isolated and operationally linked as single or multiple copies to a reporter gene for the measurement of activity of a HIF-α polypeptide that varies in accordance with the activity of a HIF hydroxylase.

The activity of genes or gene products that are regulated by a HIF-α polypeptide in accordance with the activity of a HIF hydroxylase affects cellular, organ, and animal physiology in a manner that provide further aspects of the invention. Thus a farther embodiment of the invention provides for assays that utilise a specific functional response that is regulated in accordance with the activity of a HIF-α polypeptide in accordance with the activity of a HIF hydroxylase. Such responses include the uptake rate of glucose or glucose analogues that are not metabolized, the ingrowth of blood vessels by angiogenesis, the activity of a carbonic anhydrase enzyme. It is recognised that many other responses that operate at a cellular or systemic level are controlled by the activity of a HIF-α polypeptide in accordance with the activity of a HIF hydroxylase and may be utilized as assays of the said HIF hydroxylase activity in further aspects of the invention.

A HIF-α polypeptide that is a substrate for a HIF hydroxylase may be fused to a further polypeptide so as to cause the activity of the said HIP hydroxylase to regulate the activity of the fusion peptide. Accordingly a further form of the invention provides for the assay of the activity of a fusion polypeptide. In the preferred form such a fusion polypeptide may contain the whole of part of a HIF-α polypeptide, particularly including Asn 803, or the CAD domain. The Gal4 DNA binding domain including the amino acids 1-143 together with the Gal binding upstream activating sequence (UAS) is an example of such a transcription factor and cognate DNA response element whose operation can be assayed by those skilled in the art.

Test Compounds

Compounds which may be screened using the assay methods described herein may be natural or synthetic chemical compounds used in drug screening programmes. Extracts of plants, microbes or other organisms, which contain several characterised or uncharacterised components may also be used.

Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

Potential inhibitor compounds may be polypeptides, small molecules such as molecules from commercially available combinatorial libraries, or the like. Small molecule compounds which may be used include 2-oxoglutarate analogues, or HIF-α analogues, or those that incorporate features of both 2-oxoglutarate and affect HIF-α, which inhibit the action of the enzyme. Thus the invention provides the use of a compound which acts as an asparagine hydroxylase inhibitor, for the manufacture of a medicament for the treatment of a condition in a patient which requires the promotion of cell growth, such as angiogenesis. The invention also provides a method of treatment of a patient suffering from a condition which is treatable by promoting cell growth, which comprises administering to said patient an effective amount of a HIF asparagine hydroxylase inhibitor.

Potential promoting agents may be screened from a wide variety of sources, particularly from libraries of small compounds which are commercially available. Oxygen-containing compounds may be included in candidate compounds to be screened, for example 2-oxoglutarate analogues.

A test compound which increases, potentiates, stimulates, disrupts, reduces, interferes with or wholly or partially abolishes asparagine hydroxylation of HIF-α polypeptide and which may thereby modulate HIF activity, may be identified and/or obtained using the assay methods described herein.

Agents which increase or potentiate asparagine hydroxylation, may be identified and/or obtained under conditions which, in the absence of a positively-testing agent, limit or prevent hydroxylation. Such agents may be used to potentiate, increase, enhance or stimulate the function of a HIF asparagine hydroxylase, and may have an effect on cells under hypoxic conditions such as those found in tumours, in which the lack of hydroxylation leads to the accumulation of HIFα and the concomitant promotion of angiogenesis and other growth promoting events.

Methods of determining the presence of, and optionally quantifying the amount of HIF asparagine hydroxylase in a test sample may have a diagnostic or prognostic purpose, e.g. in the diagnosis or prognosis of any medical condition discussed herein (e.g. a proliferative disorder such as cancer) or in the evaluation of a therapy to treat such a condition.

In various aspects, the present invention provides an agent or compound identified by a screening method of the invention to be a modulator of HIFα asparagine hydroxylation e.g. a substance which inhibits or reduces, increases or potentiates the asparagine hydroxylase activity of a HIF hydroxylase.

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

Selectivity

It may also be advantageous to modulate HIF asparagine hydroxylase selectively, as a single target, or in selected hydroxylase groups as well as an entire family. Agents which modulate HIF asparagine hydroxylase activity are therefore preferably specific i.e. they have an increased or enhanced effect on a HIF asparagine hydroxylase relative to other 2OG dependent oxygenases.

Assay methods as described herein may therefore further comprise contacting the test compound with one or more 2OG dependent oxygenases under conditions in which said 2OG dependent oxygenases are normally active and determining activity of said oxygenases. A difference in activity in the presence relative to the absence of test compound is indicative of the test compound modulating the activity of the one or more 2OG dependent oxygenases.

A test compound which provides increased or enhanced modulation of a HIF asparagine hydroxylase, relative to the one or more 2OG dependent oxygenases shows selectivity or specificity for the HIF hydroxylase.

2OG dependent oxygenases may include for example, clavaminte synthase, deacetoxycephalosporin C synthase, collagen-prolyl-4-hydroxylase, collagen prolyl-3-hydroxylase, lysyl hydroxylase, aspartyl hydroxylase, phytanoyl coenzyme A hydroxylase or gamma-butyrobetaine hydroxylase. 2OG dependent oxygenases may be mammalian, preferably human polypeptides.

Human 2OG oxygenases for which it may be desirable not to inhibit when modulating HIF asparagine hydroxylase activity include AlkB, collagen prolyl hydroxylases, lysine hydroxylases, the aspartyl/asparagine hydroxylase known to hydroxylate endothelial growth factor domains, phytanoyl CoA hydroxylase, gamma-butyrobetaine hydroxylase, trimethyl lysine hydroxylase, HIF prolyl hydroxylase isoforms including PHD1, PHD2, PHD3, and enzymes closely related to FIH including those proteins in the SWALL database that are referenced by the following numbers: Q9NWJ5, Q8TB10, Q9Y4E2, O95712, Q9H8B1, Q9NWT6 in *Homo sapiens*, and Q91W88 and Q9ER15 in *Mus musculus* and homologues of these enzymes. It is also recognised that in some circumstances it may be advantageous to inhibit FIH and one or more of the aforementioned enzymes, in particular one or more of the HIF prolyl hydroxylase isoforms. Further, in inhibiting some of the above enzymes it may be advantageous not to inhibit FIH and the methods can be used in a method for discovering PHD inhibitors that are not inhibitors of FIH.

The invention provides for the use of such selective inhibitors of HIF asparagine hydroxylases in the manufacture of a medicament for the treatment of a condition associated with reduced HIF activity.

In alternative aspects of the present invention, the assays can be used to establish whether agents which have been identified as inhibitors or activators of other 2OG dependent oxygenases are specific for such oxygenases, or at least do not affect HIF asparagine hydroxylase. In particular the effect of agents which act on the activity of HIF asparagine hydroxylase while not affecting the related HIF prolyl hydroxylase, or vice versa, can be established. Thus, the assays may be carried out using agents or modifications of agents which have been identified as inhibitors of a 2OG dependent oxygenase, such as collagen prolyl hydroxylase to identify whether such an agent is specific for collagen prolyl hydroxylase and is not active or shows reduced activity against HIF hydroxylases and in particular their asparagine hydroxylase activity.

Therapeutic Appplications

A compound, substance or agent which is found to have the ability to affect the hydroxylase activity of a HIF asparagine hydroxylase, has therapeutic and other potential in a number of contexts, as discussed. For therapeutic treatment, such a compound may be used in combination with any other active substance, e.g. for anti-tumour therapy another anti-tumour compound or therapy, such as radiotherapy or chemotherapy.

An agent identified using one or more primary screens (e.g. in a cell-free system) as having ability to modulate the HIFα asparagine hydroxylation activity of a HIF hydroxylase may be assessed further using one or more secondary screens. A secondary screen may involve testing for an increase or decrease in the amount of HIF-α or HIF activity, for example as manifest by the level of a HIF target gene or process present in a cell in the presence of the agent relative to the absence of the agent.

A HIF hydroxylase or a HIF polypeptide may be used in therapies which include treatment with full length polypeptides or fragments thereof, or otherwise modified polypeptides (e.g. to enhance stability or ensure targeting, including in conjunction with other active agents such as antibodies. For example, mutation of HIF-1α to replace Asn 803 with another amino acid residue may prevent hydroxylation and thus promote interaction of HIF-α with p300 and stimulate transcriptional activation.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilization of the active agent. As noted below, a composition according to the present invention may include in addition to an modulator compound as disclosed, one or more other molecules of therapeutic use, such as an anti-tumour agent.

Products Obtained by Assays of the Invention

The invention further provides compounds obtained by assay methods of the present invention, and compositions comprising said compounds, such as pharmaceutical compositions wherein the compound is in a mixture with a pharmaceutically acceptable carrier or diluent. The carrier may be liquid, e.g. saline, ethanol, glycerol and mixtures thereof, or solid, e.g. in the form of a tablet, or in a semi-solid form such as a gel formulated as a depot formulation or in a transdermally administerable vehicle, such as a transdermal patch.

The invention further provides a method of treatment which includes administering to a patient an agent which interferes with the hydroxylation of the asparagine target residue of an HIFα polypeptide by a HIF hydroxylase. Such agents may include inhibitors of asparaginyl hydroxylase activity.

The therapeutic/prophylactic purpose may be related to the treatment of a condition associated with reduced or suboptimal or increased HIF levels or activity, or conditions in which have normal HIP levels, but where an modulation in HIF activity such as an increase or decrease in HIF activity is desirable such as:

(i) ischaemic conditions, for example organ ischaemia, including coronary, cerebrovascular and peripheral vascular insufficiency. The therapy may be applied in two ways; following declared tissue damage, e.g. myocardial infarction (in order to limit tissue damage), or prophylactically to prevent ischaemia, e.g. promotion of coronary collaterals in the treatment of angina.
(ii) wound healing and organ regeneration
(iii) auto-, allo-, and xeno-transplantation.
(iv) systemic blood pressure
(v) cancer; HIFα is commonly up-regulated in tumour cells and has major effects on tumour growth and angiogenesis.
(vi) inflammatory disorders.
(vii) pulmonary arterial blood pressure, neurodegenerative disease.
(viii) diabetes Modulating HIF asparaginyl hydroxylase activity in a person, an organ, or a group of cells may be exploited in different ways to obtain a therapeutic benefit.

(a) Non cell autonomous: The HIF system is used by cells to influence the production of substances which signal to other cells. These signals may then have effects at (i) a distant site (for example erythropoietin acts on the bone marrow) or (ii) locally (angiogenic growth factors increase the local formation of blood vessels). Manipulating non cell-autonomous behaviour via altering hydroxylase activity is therefore useful in the treatment of anaemia, and local ischaemia, for example in the eye, brain, heart and limbs. Many other signals that are involved in aspects of physiological homeostatis may be, or are known to be, adjusted by HIF activation. Consequently, altering HIF asparaginyl hydroxylase activity may be used to potentiate or initiate a helpful response for a therapeutic benefit, or to prevent or ameliorate a harmful response. For example, this approach can be used to alter appetite, or blood pressure in the systemic or pulmonary beds.

(b) Cell autonomous: the HIF system is also used by cells to regulate cellular metabolism, and decisions concerning differentiation, proliferation and apoptosis. Therefore manipulating the HIF system can be used to alter the viability and behaviour of cells. An increase cell viability can be achieved by increasing HIF activation, for example in an ischaemic tissue. This approach can also be used in improving pancreatic beta cell viability as a way of ameliorating diabetes, or of improving the viability or function of a group or groups of neurons in Parkinson's disease, motorneurone disease or forms of dementia. In a different approach, the HIF signal can be manipulated to prevent a group of cells proliferating, or to promote its death or differentiation. For example transient activation of the HIF system in a malignant tumour can be used to provoke death of a substantial number of tumour cells.

Pharmaceutical Compositions

In various further aspects, the present invention thus provides a pharmaceutical composition, medicament, drug or other composition for such a purpose, the composition comprising one or more agents, compounds or substances as described herein, including HIF asparagine hydroxylase inhibitors, the use of such an composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:

(a) identifying an agent by an assay method of the invention; and
(b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

The agent may be used as sole active agent or in combination with one another or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased HIF levels or activity. The condition may, for example, be selected from the group consisting of ischaemia, wound healing, auto-, allo-, and xeno-transplantation, systemic high blood pressure, cancer, and inflammatory disorders.

Gene Therapy

The HIF asparagine hydroxylases of the present invention can be used to promote or enhance hydroxylation of HIF-α in target cells. Such promotion of hydroxylation may therefor reduce interaction with p300 and reduce transcription activation. This will be of assistance in reducing angeogenesis and effect other apoptotic and proliferative responses in target cells. Thus, in accordance with this aspect of the invention a nucleic acid encoding a HIF asparagine hydroxylase may be provided to target cells in need thereof.

Where the substances are peptides or polypeptides, they may be produced in the target cells by expression from an encoding nucleic acid introduced into the cells, e.g. from a viral vector. The vector may be targeted to the specific cells to be treated, or it may contain regulatory elements which are switched on more or less selectively by the target cells.

Nucleic acid encoding a substance e.g. a peptide able to modulate, e.g. interfere with, asparagine hydroxylation of HIFα by a HIF hydroxylase, may be used in methods of gene therapy, for instance in treatment of individuals, e.g. with the aim of preventing or curing (wholly or partially) a disorder.

Nucleic acid encoding a HIF asparagine hydroxylase as described herein may also be used in the anti-sense regulation of the HIF hydroxylase activity. Down-regulation of expression of a gene encoding a HIF hydroxylase may be achieved using anti-sense technology, or RNA interference.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Smith et al, (1988) *Nature* 334, 724-726. Antisense technology is also reviewed in Flavell, (1994) *PNAS USA* 91, 3490-3496.

The complete sequence corresponding to the reverse orientation of the coding sequence need not be used. For example, fragments of sufficient length may be used. It is a routine matter for the person skilled in the art to screen fragments of various sizes and from various parts of the coding sequence to optimise the level of anti-sense inhibition. It may be advantageous to include the initiating methionie ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than 500 nucleotides are preferable where possible.

Anti-sense oligonucleotides may be designed to hybridise to the complementary sequence of nucleic acid, pre-mRNA or mature mRNA, interfering with the production of a HIF hydroxylase encoded by a given DNA sequence (e.g. either native polypeptide or a mutant form thereof), so that its expression is reduce or prevented altogether. Anti-sense techniques may be used to target a coding sequence; a control sequence of a gene, e.g. in the 5' flanking sequence, whereby the anti-sense oligonucleotides can interfere with control sequences. Anti-sense oligonucleotides may be DNA or RNA and may be of around 14-23 nucleotides, particularly around 15-18 nucleotides, in length. The construction of antisense sequences and their use is described in Peyman and Ulman, Chemical Reviews, 90:543-584, (1990), and Crooke, Ann. Rev. Pharmacol. Toxicol., 32:329-376, (1992).

It may be preferable that there is complete sequence identity in the sequence used for down-regulation of expression of a target sequence, and the target sequence, though total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence.

The sequence need not include an open reading frame or specify an RNA that would be translatable. It may be preferred for there to be sufficient homology for the respective sense RNA molecules to hybridise. There may be down regulation of gene expression even where there is about 5%, 10%, 15% or 20% or more mismatch between the sequence used and the target gene.

Other approaches to specific down-regulation of genes which may be used to modulate HIF asparagine hydroxylase expression are well known, including the use of ribozymes designed to cleave specific nucleic acid sequences. Ribozymes are nucleic acid molecules, actually RNA, which specifically cleave single-stranded RNA, such as mRNA, at defined sequences, and their specificity can be engineered. Hammerhead ribozymes may be preferred because they recognise base sequences of about 11-18 bases in length, and so have greater specificity than ribozymes of the Tetrahymena type which recognise sequences of about 4 bases in length, though the latter type of ribozymes are useful in certain circumstances. References on the use of ribozymes include Marschall, et al. Cellular and Molecular Neurobiology, 1994. 14(5): 523; Hasselhoff, Nature 334: 585 (1988) and Cech, J. Amer. Med. Assn., 260: 3030 (1988).

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired peptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors in gene therapy other known methods of introducing nucleic acid into cells includes mechanical techniques such as microinjection, transfer mediated by liposomes and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

In various further aspects, the present invention thus provides a pharmaceutical composition, medicament, drug or other composition for use in a method of treating a medical condition described above, the composition comprising an isolated nucleic acid molecule as described herein, the use of such an composition in a method of medical treatment, a method comprising administration of such a composition to a patient, e.g. for treatment (which may include preventative treatment) of a medical condition as described above, use of such an agent compound or substance in the manufacture of a composition, medicament or drug for administration for any such purpose, e.g. for treatment of a condition as described herein, and a method of making a pharmaceutical composition comprising admixing such an agent, compound or substance with a pharmaceutically acceptable excipient, vehicle or carrier, and optionally other ingredients.

Use of Polypeptides

Another aspect of the present invention provides the use of a HIF hydroxylase as described herein or a fragment thereof for the asparagine hydroxylation of an HIF polypeptide, or an asparagine-containing substrate of HIF hydroxylase.

In particular, the present inventions have established that FIH hydroxylates an asparagine residue in HIF-α, but does not appear to have activity in hydroxylating an aspartic acid residue. Accordingly, polypeptides of the invention, that is SEQ ID NO: 2 and variants thereof as described above, may be used to specifically hydroxylate asparagine residues in a substrate with little or no hydroxylation of aspartic acid.

A HIF asparagine hydroxylase polypeptide according to the present invention can also be used to identify additional substrates of HIF hydroxylases. For example, peptides which have either previously been demonstrated to be hydroxylated by other hydroxylases, or other peptides may be brought into contact with a HIF hydroxylase according to the present invention and monitoring for asparagine hydroxylation of such peptides. Any suitable conditions may be selected including the provision of agents and co-factors known to enhance hydroxylation by the hydroxylases of the present invention. Hydroxylation of the substrate may be monitored by any suitable method including monitoring levels of co-factors or by products of hydroxylation.

Various further aspects and embodiments of the present invention will be apparent to those skilled in the art in view of the present disclosure.

Certain aspects and embodiments of the invention will now be illustrated by way of example and with reference to the figures described below.

DESCRIPTION OF THE FIGURES

FIG. 1b: FIH modulates HIF-1α CAD binding to the CH1 domain of p300. The autoradiograph shows capture of $^{35}S$-labeled CH1 by HIF-1α CAD that had or had not been pre-incubated with recombinant FIH. Pre-incubation with FIH strikingly reduced ability of HIF-1α CAD to capture CH1 (compare lanes 1 and 2). Inclusion of N-oxaloylglycine in the FIH/HIF-1α CAD reaction step inhibited the effect of FIH. Binding of CH1 to N803A mutant HIF-1α CAD that is constitutively active was unaffected by pre-incubation with FIH (lanes 4 and 5).

FIG. 2a: Sequence alignment of CAS1 (clavaminic acid synthase 1, Q05581); PHD3 (prolyl hydroxylase domain containing protein 3, Q9H6Z9); FIH1 (factor inhibiting HIF-1, Q969Q7); PMI (phosphomannose isomerase Type II, P34948), comparing conserved secondary structure and binding motifs. The crystallographically assigned secondary structure of CAS1 is indicated above the alignment and PMI below the alignment, jellyroll β-strands are numbered. The α-helices and β-strands not in the jellyroll can also be seen. Note the common presence of an insert between β-strands 4 and 5 of the jellyroll in FIH, also present in CAS 1 and taurine dioxygenase (not shown), which define a subfamily of 2-OG dioxygenases. The known/predicted metal-binding ligands are indicated by a triangle. In reported enzyme:Fe(II):2-OG structures the 5-carboxylate of 2-OG forms an electrostatic interaction with the side-chain of an arginine residue (indicated by a triangle). FIH does not possess either of the $RX_3T$ (as in the PHDs) or RXS motifs identified as binding the 2-OG 5-carboxylate, nor a lysine in an analogous position to the arginine of these motifs (as in procollagen prolyl hydroxylase). In FIH, Thr-290 and Thr-292, located on the 8$^{th}$ jellyroll β-strand, may be involved in 2-OG binding.

EXAMPLES

Experimental Procedures

Figure 1A:
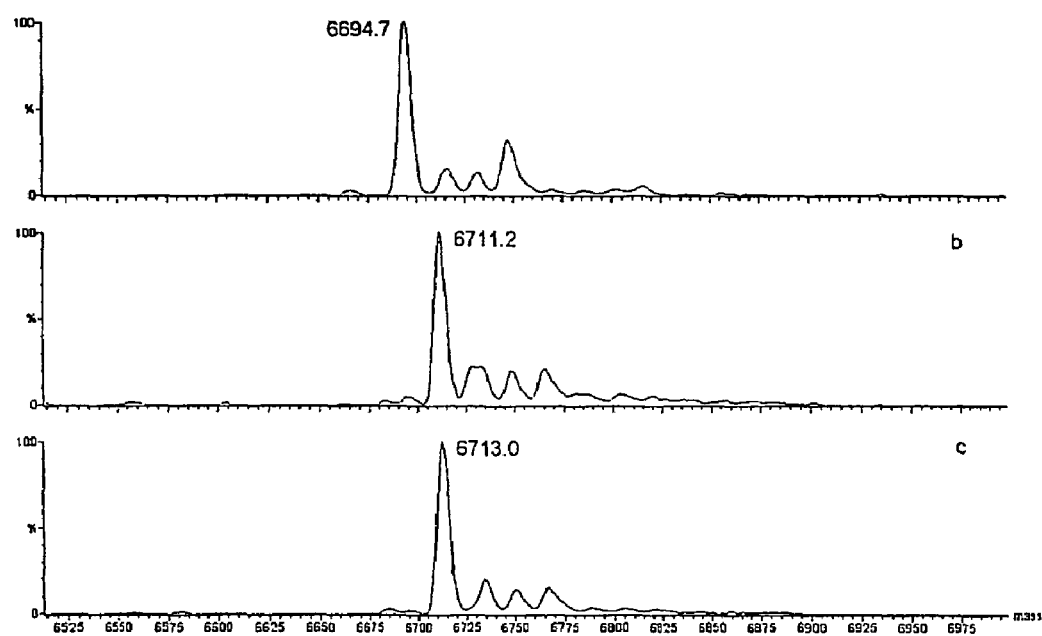
FIG. 1a: Electrospray ionisation mass spectra of HIF-1α 775-826 demonstrating the incorporation of oxygen from dioxygen into product: a) HIF-1α 775-826 before reaction, calculated mass 6697.31 Da, observed mass (MH+)=6694.7 Da; b) peptide isolated from reaction under norm-oxic ($^{16}O_2$) conditions, mass increase=16.5 Da; c) peptide isolated from reaction under $^{18}O_2$ atmosphere, mass increase=18.3 Da.

Cloning, expression and purification of fih/FIH—The fih gene was PCR amplified from Image clone 4138066 and subcloned as an Nde I/BamH I fragment into the pET28a(+) vector (Novagen) in order to generate an N-termilal His$_6$-tagged FIH fusion protein. Primers used were: forward; 5'-gg-gaattccatatggcggcgacagcggcg-3'(SEQ ID NO:4), reverse; 5'cgcggatccctagttgtatcggccc-3'(SEQ ID NO:5). Following amplification the integrity of fih was confirmed by DNA sequencing. The fih/pET28a(+) construct was transformed into *Escherichia coli* BL21(DE3) and grown at 37° C. in 2TY media containing 30 μg/ml kanamycin and was induced with isopropyl-1-(D)-thiogalactoside (IPTG). The N-terminal His$_6$-tagged FIH fusion protein was purified using nickel affinity chromatography (Novagen) and the N-terminal His$_6$ tag removed from FIH by cleavage with thrombin. Size exclusion chromatography (Superdex S75) yielded FIH of >95% purity by SDS-PAGE analysis. Electrospray ionisation MS revealed the mass of the isolated FIH was consistent with that expected from its predicted amino acid sequence (observed 40,556 Da, calculated 40,567Da).

Cloning expression and purification of HIF-1α fragments—The desired segments of Human HIF-1α were cloned directly as Sac II/Asc I fragments from pcDNA3 vectors (O Rourke et al (1999) J. Biol Chem 274, 2060-2071) into a modified version of pGEX-6P-1 (Amersham Biosciences) in order to generate N-terminal glutathione S-transferase (GST) tagged fusion proteins. The constructs were transformed into *E. coli* BL21(DE3) and grown at 37° C. in 2TY media containing 100 μg/ml ampicillin and were induced with IPTG. The GST-tagged fusion proteins were purified using Glutathione Sepharose™ 4B resin (Amersham Biosciences). The GST tag was removed from the HIF-1α fragments when required by PreScission™ Protease treatment. Size exclusion chromatography (Superdex S75) yielded >95% pure protein by SDS-PAGE analysis. His$_6$-tagged sections of HIF-1α were prepared as described in Epstein et al, 2001. Cell, 107 43-54.

Mutagenesis studies of HIF-1α 775-826—Mutant GST HIF-1α 775-826 isoenzymes were produced from the wild-type construct using the Quikchange system (Stratagene). The primers for each of the asparagine mutations were: N803A;

```
forward:                                    (SEQ ID NO:6)
5'-gttatgattgtgaagttgctgctccatatacaaggc-3', reverse:                                    (SEQ ID NO:7)
5'-gtataggagcagcaacttcacaatcataactgg-3'
N803Q;
```

```
forward:                                    (SEQ ID NO:8)
5'-gttatgattgtgaagttcaagctcctatacaaggc-3' reverse:                                    (SEQ ID NO:9)
5'-gtataggacgttgaacttcacaatcataactgg-3',
N803E;

forward:                                    (SEQ ID NO:10)
5'-gttatgattgtgaagttgaagctcctatacaaggc-3' reverse:                                    (SEQ ID NO:11)
5'-ttgtataggagcttcaacttcacaatcataactgg-3', N803D;
forward:                                    (SEQ ID NO:12)
gttatgattgtgaagttgatgctcctatacaaggc-3', reverse;                                    (SEQ ID NO:13)
5'-ttgtataggagcatcaacttcacaatcataactgg.
Mutations were confirmed by DNA sequencing.
```

FIH assays—Assays for decarboxylation of 2-OG were performed using radiolabelled 2-OG (New England Nuclear) as reported in Epstein et al supra. Incubations contained ascorbate, DTT, catalase, 2-OG, FIH, and substrate in 50 mM Tris/HCl pH7.4, and were carried out at 37° C. typically for 20 minutes. HPLC separations were achieved on a Phenomenex Jupiter C4 (10 cm×4.6 mm) column by using of a linear gradient of $CH_3CN$ in 0.1% TFA. For inhibition and metal dependence assays, GST HIF-1α 775-826 was used as substrate at 30 μM, and with iron(II) ammonium sulfate, cobalt (II) chloride, zinc(II) chloride, and N-oxaloylglycine at final concentrations of 0, 2, 10, 40, 80 and 200 μM. Assays under an atmosphere of $^{18}O_2$ were performed as reported in McNeill et al, Bioorg Med Chem Lett, 2002 12, 1547-1550.

GST pulldown assays—To examine for effects of FIH on HIF-1α binding to p300, the GST fusion protein expressing amino acids of HIF-1α 775-826 and the N803A mutant were exposed to recombinant FIH under conditions designed to promote the hydroxylation. N-oxaloylglycine was added to 5 mM when required. Glutathione Sepharose beads were added for 40 minutes at 25° C. and then washed with 50 mM Tris/HCl pH 7.4, 0.5% NP40, 150 mM NaCl and 1 mM DTT. The beads bearing the treated GST HIF fusion proteins were mixed with $^{35}S$ labeled CH1-p300 (pcDNA3 Gal-p300-CH1 encoding amino acids 300-528 of p300) produced in rabbit reticulocyte lysate. Binding was performed for 1 hour at 25° C. and the beads were then-washed in the same buffer. The bound proteins were eluted in SDS running buffer and analyzed by SDS-PAGE and autoradiography.

Fluorescence polarisation assay—Assays for hydroxylation of HIF polypeptide can be carried out in 50 mM Tris/HCl pH7.5. Incubations contain 4 mM ascorbic acid, 1 mM DTT, 80 microM 2OG, polypeptide, 468 nM GST-p300 complex (where GST is glutathion S transferase, a purification aid), 15 microM iron(II), and 0.3 nM HIF hydroxylase. Incubation may be at 29° Celsius. A graph can be plotted of data in real time from the incubation of a HIF hydroxylase with a labelled (Cy5 fluorescence dye) HIF fragment in the presence of p300 to which hydroxylated peptide binds resulting in an increase in anisotropy.

FIH is a HIF-α CAD hydroxylase—Preliminary analysis of the predicted FIH amino acid sequence in light of the sequences for 2-OG oxygenases of known structure and function suggested that FIH contained the conserved HX(D/E) . . .H 'facial triad' of residues that binds the Fe(II) cofactor. Given the reported interaction of FIH with the C-terminal activation domain of HIF-1α and its ability to downregulate transactivation we considered that FIH might function as the Asn-803 hydroxylase.

N-Terminally His$_6$-tagged FIH gene was therefore produced in E. coli BL21(DE3) and purified to >95% purity. HIF-1α polypeptides encompassing all three identified sites of hydroxylation were then examined as putative substrates for purified recombinant FIH (Table 1, entries 1-6), using an assay that monitors decarboxylation of 2-OG. The results clearly indicate that there was no FIH mediated hydroxylation of those HIF fragments previously shown to be substrates for the PHD isozymes thereby implying that FIH is not a HIF prolyl hydroxylase (Table 1, entries 4-6). In contrast, $CO_2$ production was strikingly stimulated in the presence of HIF-1α fragments containing the C-terminal activation domain (CAD, Table 1, entries 1-3). Both GST-fused and free forms of a polypeptide encompassing the human HIF-1α CAD (residues 775-826) were observed to cause significant stimulation of FIH mediated 2-OG turnover. A high ratio (>10:1) of prime substrate coupled:uncoupled 2-OG turnover was observed in the case of the free 775-826 substrate, and preliminary kinetic parameters for this peptide obtained using the 2-OG turnover assay were $K_m$(peptide)=10 μM, $K_m$(2-OG)=10 μM, $V_{max}$=0.3 μmol/min/mg.

TABLE 1

Substrate selectivity of FIH with HIF-1α polypeptides. FIH was incubated with proteins containing the three known hydroxylation sites (Pro-402, Pro-564, Asn-803) in HIF-1α. Column 3 indicates activity of polypeptides as assayed by $CO_2$ release under the standard assay conditions. Column 4 shows the activity of each substrate relative to the activity of 775-826 peptide as a substrate under the same conditions. See Experimental for assay details.

| Entry | Substrate | $CO_2$ released (nmol) | % activity relative to 775-826 peptide |
|---|---|---|---|
| 1 | HIF-1α 775-826 | 2.8 | 100 |
| 2 | GST HIF-1α 775-826 | 2.7 | 96 |
| 3 | GST HIF-1α 577-826 | 0.81 | 67 |
| 4 | GST HIF-1α 530-652 | 0.05 | 1.8 |
| 5 | His$_6$-HIF-1α 344-503 | <0.001 | <0.01 |
| 6 | His$_6$-HIF-1α 530-698 | <0.001 | <0.01 |
| 7 | GST HIF-1α 775-826 N803D | 0.22 | 7 |
| 8 | GST HIF-1α 775-826 N803A | <0.001 | <0.01 |
| 9 | GST HIF-1α 775-826 N803E | <0.001 | <0.01 |
| 10 | GST HIF-1α 775-826 N803Q | <0.001 | <0.01 |

Since the 2-OG turnover assay does not directly measure oxidation of the prime substrate, unequivocal demonstration of FIH mediated hydroxylation was sought from mass spectrometric analyses. Using HIF-1α 775-826 peptide as a substrate under normoxic conditions, an increase in mass of 16Da was observed after HPLC isolation of product (FIG. 1a, panels a and b). The results demonstrate that FIH is a 2-OG dependent hydroxylase that modifies the HIF-1α CAD. To test whether this activity regulates the interaction with the p300 co-activator, GST-fused HIF-1α CAD was exposed to purified recombinant FIH under conditions that support decarboxylation of 2-OG, purified, and assayed for the ability to interact with $^{35}$S-labelled CH1 by GST pulldown assay. FIG. 1b shows that pre-treatment with FIH greatly reduced the ability of the HIF-1α CAD polypeptide to interact with CH1 (compare lanes 1 and 2).

Following previous MS/MS assignment of Asn-803 as the modified residue in the HIF-1α CAD, we constructed a series a mutations at this site and performed further 2-OG decarboxylation and interaction assays using the mutant polypeptides. Mutation of Asn-803 in GST HIF-1α 775-826 to alanine abolished all activity in the 2-OG decarboxylation assay (Table 1, entries 8-10), and prevented modulation of CH1 binding in the interaction assay (FIG. 1b, lanes 4 and 5). Mutation to glutamine and glutamate also abolished activity, whilst an Asp-803 mutant still supported some 2-OG turnover, but only at a maximum of 7% of the analogous Asn-803 substrate (Table 1, entry 7).

Taken together these results demonstrate that FIH is the dioxygen requiring Asn-803 hydroxylase that controls HIF-α C-terminal transactivation by regulating the interaction with the CH1 domain of p300. The clear preference of FIH for an asparaginyl rather than an aspartyl residue as substrate contrasts with the previously reported human Asp/Asn hydroxylase which catalyses hydroxylation at the β-carbon of both aspartyl and asparaginyl residues. This observation raises the possibility that FIH mediated hydroxylation does not occur at the β-carbon of Asn-803 but at another atom. Oxidation of either the α-carbon or the carbonyl oxygen of the primary amide seems unlikely given the relative lack of activity of the Asp-803 and other mutants and likely instability of the putative products. It is more likely that nitrogen of the primary amide is hydroxylated to give a hydroxamic acid ($CH_2CONHOH$). The available NMR data suggests that such a modification would be disruptive to the interaction between CAD and p300.

Further characterization of FIH activity—To explore the mechanism of FIH and its relationship to the characteristics of in vivo HIF activation, in vitro analyses of FIH using the purified recombinant protein were performed. Analyses revealed that the purified recombinant FIH contained ca. 1 metal ion per protein, consistent with the operation of a mono-iron catalytic site (unpublished data). FIH was inhibited by N-oxaloylglycine, a known inhibitor of the PHD isozymes and other 2-OG oxygenases, both in bioassays of CH1 capture by HIF-1α CAD (FIG. 1b compare lanes 2 and 3) and in vitro kinetic assays ($IC_{50}$, 25 μM). Cobalt (II) also inhibited recombinant FIH activity ($IC_{50}$, 10 μM), explaining the ability of these substances to regulate HIF-1α CAD activity. Interestingly addition of exogenous iron (II) to the purified FIH/HIF-1α CAD assay produced no further increase in activity, implying relatively tight metal binding by FIH. This may reflect the ability of the hydroxylated asparagine product to chelate iron. Because of the relationship of FIH to the zinc (II) binding proteins from the cupin family (see below) we also tested the action of zinc (II) and found similar inhibition to that with cobalt (II) ($IC_{50}$, 10 μM). Though zinc (II) does not induce a HIF transcriptional response, recent studies have demonstrated that it does stabilize HIF-1α, but blocks transactivation by inducing alternative splicing to a shortened form that lacks the CAD. Though the physiological relevance of these findings is still unclear it therefore seems likely that zinc (II) inhibits both FIH and the PHD enzymes.

The requirement of FIH for dioxygen as a co-substrate indicates that, like the PHD isozymes, FIH may act as a cellular oxygen sensor. Indeed, when assayed under conditions of graded reduction of atmospheric oxygen, FIH demonstrated large and progressive reductions in HIF-1α CAD linked 2-OG decarboxylation below ca. 5% $O_2$. This suggests that, as for PHD1, activity is limited by oxygen concentrations in the physiological range. To explore further the interaction with dioxygen, the origin of the incorporated oxygen atom in the product was investigated by incubation under an atmosphere of $^{18}O_2$ gas followed by mass spectrometric analysis. The results reveal the source of the oxygen in the hydroxylated product to be >98% derived from dioxygen (FIG. 1a, panel c), demonstrating a direct interaction between FIH and dioxygen, as shown for PHD1 and procollagen prolyl hydroxylase. These results contrast with similar incorporation experiments with microbial 2-OG oxygenases where incorporation of oxygen from water as well as dioxygen is observed. The exchange process has been proposed to occur via binding of water to a pentacoordinate ferryl species[Fe (IV)=O<->Fe(III)-O]. In the case of FIH and PHD1, it may be that the presence of a large peptide substrate at the active site blocks access of water so preventing exchange.

Biological and structural implications—The involvement of a further member of the 2-OG oxygenase superfamily, distinct from the PHD isozymes, in the regulation of HIF transactivation raises several biological issues. First it defines another link between the availability of dioxygen and HIF activity that may help shape the physiological characteristics of the transcriptional response to hypoxia. Second it provides an explanation for the characteristic action of cobalt in mimicking the effect of hypoxia on both the isolated degradation and activation domains of HIF-α subunits. Third it provides a further target for the development of therapeutic agents that augment HIF activity in ischaemia/hypoxic disease. Fourth the reported interactions of FIH with both histone deacetylases and pVHL suggests that these proteins may be involved in additional oxygen regulated processes that affect the HIF transcriptional response or other pathways.

Our findings also raise interesting structural and evolutionary issues with respect to the 2-OG oxygenases and related enzymes. Sequence comparisons reveal that FIH, like the PHD isozymes, employs a 2-His-1-carboxylate facial triad formed from a conserved HX(D/E) . . . H motif, as found in other 2-OG oxygenases. Together with crystallographic insights and secondary structure predictions, the analyses imply that FIH possesses the jellyroll β-sheet core (double stranded β-helix) common to other 2-OG oxygenases. They also reveal that FIH possesses a ca. 40 residue insert between β-strands 4 and 5 of the 8-stranded jellyroll motif (FIG. 2a) and suggest that the structure of the FIH will be significantly different to the PHD isozymes, which are closely related to one another.

Though kinetic analyses clearly demonstrate a requirement of FIH for 2-OG, an unusual feature of FIH concerns the identity of residues involved in binding the 5-carboxylate of 2-OG. The analyses imply that FIH does not possess an arginine or lysine residue, located on β-strand 8 of the jellyroll, that is involved in binding the 2-OG 5-carboxylate present in the PHDs and many other 2-OG oxygenases (FIG. 2a).

Thus, FIH probably constitutes the first member of a new structural subfamily of 2-OG oxygenases and the development of inhibitors selective for FIH versus the PHD isozymes or vice versa should be possible.

Figure 2B:
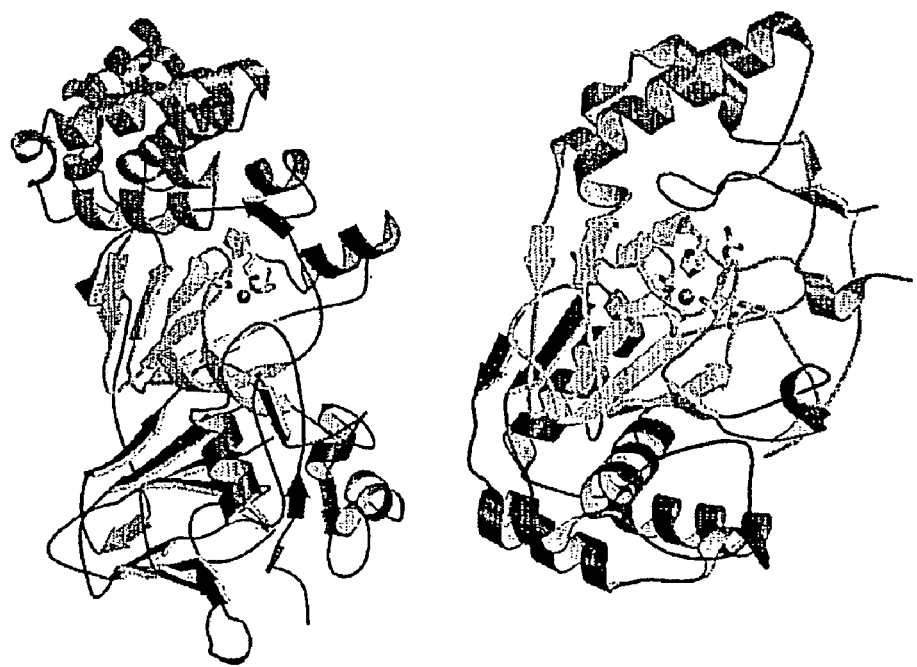
FIG. 2b: Comparison of structures of phosphomannose isomerase complexed with zinc (left) and clavaminic acid synthase complexed with Fe(II), 2-OG and (L)-N-α-acetylarginine substrate (right). The core jellyroll motif, the insert to this jellyroll motif and other secondary structure can be seen. The analogously located metal-binding residues and the two substrates of CAS1 can also be seen. Note PMI possess an extended insert (~115 residues) to the jellyroll motif as in CAS1 and predicted for FIH.

Mahon et al. used BLAST searches to identify proteins with sequence similarity to FIH. One of these (Genbank AF 168362.1) is a JmjC homology region, present in the jumonji transcription factors, which have been identified as members of the cupin structural superfamily. The identification of FIH as an Fe(H) dependent oxygenase inhibited by Zn(II) prompted us to compare crystal structures from the 2-OG and cupin superfamilies. These analyses revealed a striking similarity between the cores of the 2-OG oxygenases, exemplified by clavaminic acid synthase (CAS1[2]), and the cupin superfamily, exemplified by phosphomannose isomerase (PMI[3]) (27), which, together with the presence of conserved motifs, suggests the 2-OG oxygenases belong to the cupin superfamily (FIG. 2b). Further, the HXH . . . H metal binding motif is well established within the cupin superfamily (e.g. in quercetin 2,3-dioxygenase) and is modified to a QXH . . . H motif in the case of Type II PMI. Interestingly, the JmjC transcription factors have been implicated in cell growth and heart development, and possess a conserved HX(D/E) . . . H motif as in the 2-OG oxygenases, suggesting that, like FIH and the PHD isozymes, they might be iron oxygenases involved in the regulation of transcription.

The invention claimed is:

1. A method of identifying an agent which inhibits hydroxylation of hypoxia inducible factor (HIF), the method comprising:

introducing into a cell that expresses a substrate of HIF asparagine hydroxylase a vector expressing HIF asparagine hydroxylase, the HIF asparagine hydroxylase having the amino acid sequence of SEQ ID NO: 2, or a variant or fragment thereof having at least 95% identity to the amino acid sequence of SEQ ID NO: 2 and having HIF asparagine hydroxylase activity;

contacting the cell with a test substance under conditions in which asparagine in the substrate is hydroxylated in the absence of the test substance; and determining hydroxylation of the substrate, wherein a decrease in the hydroxylation of the asparagine in the substrate in the presence of the test substance compared with the hydroxylation of the asparagine in the substrate in the absence of the test substance identifies the test substance as the agent which inhibits hydroxylation of HIF.

2. The method of claim 1, wherein the cell is a yeast cell.

3. The method of claim 1, wherein the substrate is an HIF polypeptide.

4. The method of claim 3, wherein the HIF polypeptide comprises HIF-1α, a fragment thereof comprising Asn 803 of HIF-1α, or a peptide analogue of HIF-1α or fragment thereof comprising an asparagine equivalent to Asn 803 of HIF-1α.

5. The method of claim 4, wherein the substrate comprises the CAD domain of the human HIF-1α polypeptide sequence.

6. The method of claim 4, wherein hydroxylation of Asn 803 or of the equivalent asparagine is determined.

7. The method of claim 4, wherein hydroxylation of the substrate is determined by monitoring the interaction of the HIF polypeptide with the CH1 domain of p300.

8. The method of claim 4, wherein hydroxylation of the substrate is determined by monitoring mediated transcription or expression of a reporter gene driven by a HIF regulated promoter.

9. The method of claim 4, wherein the contacting step is conducted in the presence of 2-oxoglutarate or dioxygen.

10. The method of claim 1, wherein hydroxylation of the substrate is determined by monitoring the interaction of the HIF polypeptide with the CH1 domain of p300.

11. The method of claim 1, wherein the hydroxylation of the substrate is determined by monitoring HIF mediated transcription or expression of a reporter gene driven by a HIF regulated promoter.

12. The method of claim 1, further comprising formulating an agent identified as a modulator of HIF asparagine hydroxylase with a pharmaceutically acceptable excipient.

13. The method of claim 1, wherein the contacting step is conducted in the presence of 2-oxoglutarate or dioxygen.

14. The method of claim 1, further comprising: contacting the test substance with one or more 2OG-dependent oxygenases under conditions in which the 2OG-dependent oxygenases are active; and determining the activity of the oxygenases, wherein increased modulation of a HIF asparagine hydroxylase relative to the one or more 2OG-dependent oxygenases indicates that the test compound is selective for the HIF asparagine hydroxylase.

15. A method of identifying an agent which promotes hydroxylation of hypoxia inducible factor (HIF), the method comprising:

introducing into a cell that expresses a substrate of HIF asparagine hydroxylase a vector expressing HIF asparagine hydroxylase, the HIF asparagine hydroxylase having the amino acid sequence of SEQ ID NO: 2, or a variant or fragment thereof having at least 95% identity to the amino acid sequence of SEQ ID NO: 2 and having HIF asparagine hydroxylase activity;

contacting the cell with a test substance under conditions in which asparagine in the substrate is hydroxylated in the absence of the test substance; and determining hydroxylation of the substrate, wherein an increase in the hydroxylation of the asparagine in the substrate in the presence of the test substance compared with the hydroxylation of the asparagine in the substrate in the absence of the test substance identifies the test substance as the agent which promotes hydroxylation of HIF.

16. A method of identifying an agent which inhibits hydroxylation of hypoxia inducible factor (HIF), the method comprising:

contacting a recombinant HIF asparagine hydroxylase with a test substance in the presence of a substrate of the HIF asparagine hydroxylase under conditions in which asparagine in the substrate is hydroxylated in the absence of the test substance, the HIF asparagine hydroxylase having the amino acid sequence of SEQ ID NO: 2, or a variant or fragment thereof having at least 95% identity to the amino acid sequence of SEQ ID NO: 2 and having HIF asparagine hydroxylase activity; and determining hydroxylation of the substrate, wherein a decrease in the hydroxylation of the asparagine in the substrate in the presence of the test substance compared with the hydroxylation of the asparagine in the substrate in the absence of the test substance identifies the test substance as the agent which inhibits hydroxylation of HIF.

* * * * *

SEQUENCE LISTING

<160> NUMBER OF SEQ ID NOS: 13

<210> SEQ ID NO 1
<211> LENGTH: 1050
<212> TYPE: DNA
<213> ORGANISM: Homo sapiens
<220> FEATURE:
<221> NAME/KEY: CDS
<222> LOCATION: (1)..(1050)
<223> OTHER INFORMATION:

<400> SEQUENCE: 1

```
atg gcg gcg aca gcg gcg gag gct gtg gcc tct ggc tct gga gag ccc      48
Met Ala Ala Thr Ala Ala Glu Ala Val Ala Ser Gly Ser Gly Glu Pro
1               5                   10                  15 cgg gag gag gct gga gcc ctc ggc ccc gcc tgg gat gaa tcc cag ttg      96
Arg Glu Glu Ala Gly Ala Leu Gly Pro Ala Trp Asp Glu Ser Gln Leu
            20                  25                  30 cgc agt tat agc ttc ccg act agg ccc att ccg cgt ctg agt cag agc     144
Arg Ser Tyr Ser Phe Pro Thr Arg Pro Ile Pro Arg Leu Ser Gln Ser
        35                  40                  45 gac ccc cgg gca gag gag ctt att gag aat gag gag cct gtg gtg ctg     192
Asp Pro Arg Ala Glu Glu Leu Ile Glu Asn Glu Glu Pro Val Val Leu
    50                  55                  60 acc gac aca aat ctt gtg tat cct gcc ctg aaa tgg gac ctt gaa tac     240
```

| | | | | | | | | | | | | | | | | |
|---|---|---|---|---|---|---|---|---|---|---|---|---|---|---|---|---|
| Thr | Asp | Thr | Asn | Leu | Val | Tyr | Pro | Ala | Leu | Lys | Trp | Asp | Leu | Glu | Tyr | |
| 65 | | | | 70 | | | | 75 | | | | | 80 | | | |

| ctg | caa | gag | aat | att | ggc | aat | gga | gac | ttc | tct | gtg | tac | agt | gcc | agc | 288 |
|---|---|---|---|---|---|---|---|---|---|---|---|---|---|---|---|---|
| Leu | Gln | Glu | Asn | Ile | Gly | Asn | Gly | Asp | Phe | Ser | Val | Tyr | Ser | Ala | Ser | |
| | | | | 85 | | | | | 90 | | | | | 95 | | |

| acc | cac | aag | ttc | ttg | tac | tat | gat | gag | aag | aag | atg | gcc | aat | ttc | cag | 336 |
|---|---|---|---|---|---|---|---|---|---|---|---|---|---|---|---|---|
| Thr | His | Lys | Phe | Leu | Tyr | Tyr | Asp | Glu | Lys | Lys | Met | Ala | Asn | Phe | Gln | |
| | | | 100 | | | | | 105 | | | | | 110 | | | |

| aac | ttt | aag | ccg | agg | tcc | aac | agg | gaa | gaa | atg | aaa | ttt | cat | gag | ttc | 384 |
|---|---|---|---|---|---|---|---|---|---|---|---|---|---|---|---|---|
| Asn | Phe | Lys | Pro | Arg | Ser | Asn | Arg | Glu | Glu | Met | Lys | Phe | His | Glu | Phe | |
| | | 115 | | | | | 120 | | | | | 125 | | | | |

| gtt | gag | aaa | ctg | cag | gat | ata | cag | cag | cga | gga | ggg | gaa | gag | agg | ttg | 432 |
|---|---|---|---|---|---|---|---|---|---|---|---|---|---|---|---|---|
| Val | Glu | Lys | Leu | Gln | Asp | Ile | Gln | Gln | Arg | Gly | Gly | Glu | Glu | Arg | Leu | |
| | 130 | | | | | 135 | | | | | 140 | | | | | |

| tat | ctg | cag | caa | acg | ctc | aat | gac | act | gtg | ggc | agg | aag | att | gtc | atg | 480 |
|---|---|---|---|---|---|---|---|---|---|---|---|---|---|---|---|---|
| Tyr | Leu | Gln | Gln | Thr | Leu | Asn | Asp | Thr | Val | Gly | Arg | Lys | Ile | Val | Met | |
| 145 | | | | | 150 | | | | | 155 | | | | | 160 | |

| gac | ttc | tta | ggt | ttt | aac | tgg | aac | tgg | att | aat | aag | caa | cag | gga | aag | 528 |
|---|---|---|---|---|---|---|---|---|---|---|---|---|---|---|---|---|
| Asp | Phe | Leu | Gly | Phe | Asn | Trp | Asn | Trp | Ile | Asn | Lys | Gln | Gln | Gly | Lys | |
| | | | | 165 | | | | | 170 | | | | | 175 | | |

| cgt | ggc | tgg | ggg | cag | ctt | acc | tct | aac | ctg | ctg | ctc | att | ggc | atg | gaa | 576 |
|---|---|---|---|---|---|---|---|---|---|---|---|---|---|---|---|---|
| Arg | Gly | Trp | Gly | Gln | Leu | Thr | Ser | Asn | Leu | Leu | Leu | Ile | Gly | Met | Glu | |
| | | | 180 | | | | | 185 | | | | | 190 | | | |

| gga | aat | gtg | aca | cct | gct | cac | tat | gat | gag | cag | cag | aac | ttt | ttt | gct | 624 |
|---|---|---|---|---|---|---|---|---|---|---|---|---|---|---|---|---|
| Gly | Asn | Val | Thr | Pro | Ala | His | Tyr | Asp | Glu | Gln | Gln | Asn | Phe | Phe | Ala | |
| | | 195 | | | | | 200 | | | | | 205 | | | | |

| cag | ata | aaa | ggt | tac | aaa | cga | tgc | atc | tta | ttc | cct | ccg | gat | cag | ttc | 672 |
|---|---|---|---|---|---|---|---|---|---|---|---|---|---|---|---|---|
| Gln | Ile | Lys | Gly | Tyr | Lys | Arg | Cys | Ile | Leu | Phe | Pro | Pro | Asp | Gln | Phe | |
| | 210 | | | | | 215 | | | | | 220 | | | | | |

| gag | tgc | ctc | tac | cca | tac | cct | gtt | cat | cac | cca | tgt | gac | aga | cag | agc | 720 |
|---|---|---|---|---|---|---|---|---|---|---|---|---|---|---|---|---|
| Glu | Cys | Leu | Tyr | Pro | Tyr | Pro | Val | His | His | Pro | Cys | Asp | Arg | Gln | Ser | |
| 225 | | | | | 230 | | | | | 235 | | | | | 240 | |

| cag | gtg | gac | ttt | gac | aat | ccc | gac | tac | gag | agg | ttc | cct | aat | ttc | caa | 768 |
|---|---|---|---|---|---|---|---|---|---|---|---|---|---|---|---|---|
| Gln | Val | Asp | Phe | Asp | Asn | Pro | Asp | Tyr | Glu | Arg | Phe | Pro | Asn | Phe | Gln | |
| | | | | 245 | | | | | 250 | | | | | 255 | | |

| aat | gtg | gtt | ggt | tac | gaa | aca | gtg | gtt | ggc | cct | ggt | gat | gtt | ctt | tac | 816 |
|---|---|---|---|---|---|---|---|---|---|---|---|---|---|---|---|---|
| Asn | Val | Val | Gly | Tyr | Glu | Thr | Val | Val | Gly | Pro | Gly | Asp | Val | Leu | Tyr | |
| | | | 260 | | | | | 265 | | | | | 270 | | | |

| atc | cca | atg | tac | tgg | tgg | cat | cac | ata | gag | tca | tta | cta | aat | ggg | ggg | 864 |
|---|---|---|---|---|---|---|---|---|---|---|---|---|---|---|---|---|
| Ile | Pro | Met | Tyr | Trp | Trp | His | His | Ile | Glu | Ser | Leu | Leu | Asn | Gly | Gly | |
| | | 275 | | | | | 280 | | | | | 285 | | | | |

| att | acc | atc | act | gtg | aac | ttc | tgg | tat | aag | ggg | gct | ccc | acc | cct | aag | 912 |
|---|---|---|---|---|---|---|---|---|---|---|---|---|---|---|---|---|
| Ile | Thr | Ile | Thr | Val | Asn | Phe | Trp | Tyr | Lys | Gly | Ala | Pro | Thr | Pro | Lys | |
| | 290 | | | | | 295 | | | | | 300 | | | | | |

| aga | att | gaa | tat | cct | ctc | aaa | gct | cat | cag | aaa | gtg | gcc | ata | atg | aga | 960 |
|---|---|---|---|---|---|---|---|---|---|---|---|---|---|---|---|---|
| Arg | Ile | Glu | Tyr | Pro | Leu | Lys | Ala | His | Gln | Lys | Val | Ala | Ile | Met | Arg | |
| 305 | | | | | 310 | | | | | 315 | | | | | 320 | |

| aac | att | gag | aag | atg | ctt | gga | gag | gcc | ttg | ggg | aac | cca | caa | gag | gtg | 1008 |
|---|---|---|---|---|---|---|---|---|---|---|---|---|---|---|---|---|
| Asn | Ile | Glu | Lys | Met | Leu | Gly | Glu | Ala | Leu | Gly | Asn | Pro | Gln | Glu | Val | |
| | | | | 325 | | | | | 330 | | | | | 335 | | |

| ggg | ccc | ttg | ttg | aac | aca | atg | atc | aag | ggc | cga | tac | aac | tag | | | 1050 |
|---|---|---|---|---|---|---|---|---|---|---|---|---|---|---|---|---|
| Gly | Pro | Leu | Leu | Asn | Thr | Met | Ile | Lys | Gly | Arg | Tyr | Asn | | | | |
| | | | 340 | | | | | 345 | | | | | | | | |

<210> SEQ ID NO 2
<211> LENGTH: 349
<212> TYPE: PRT
<213> ORGANISM: Homo sapiens

<400> SEQUENCE: 2

```
Met Ala Thr Ala Ala Glu Ala Val Ala Ser Gly Ser Gly Glu Pro
1               5                   10                  15

Arg Glu Glu Ala Gly Ala Leu Gly Pro Ala Trp Asp Glu Ser Gln Leu
            20                  25                  30

Arg Ser Tyr Ser Phe Pro Thr Arg Pro Ile Pro Arg Leu Ser Gln Ser
            35                  40                  45

Asp Pro Arg Ala Glu Glu Leu Ile Glu Asn Glu Glu Pro Val Val Leu
    50                  55                  60

Thr Asp Thr Asn Leu Val Tyr Pro Ala Leu Lys Trp Asp Leu Glu Tyr
65                  70                  75                  80

Leu Gln Glu Asn Ile Gly Asn Gly Asp Phe Ser Val Tyr Ser Ala Ser
                85                  90                  95

Thr His Lys Phe Leu Tyr Tyr Asp Glu Lys Lys Met Ala Asn Phe Gln
            100                 105                 110

Asn Phe Lys Pro Arg Ser Asn Arg Glu Glu Met Lys Phe His Glu Phe
            115                 120                 125

Val Glu Lys Leu Gln Asp Ile Gln Gln Arg Gly Gly Glu Glu Arg Leu
    130                 135                 140

Tyr Leu Gln Gln Thr Leu Asn Asp Thr Val Gly Arg Lys Ile Val Met
145                 150                 155                 160

Asp Phe Leu Gly Phe Asn Trp Asn Trp Ile Asn Lys Gln Gln Gly Lys
                165                 170                 175

Arg Gly Trp Gly Gln Leu Thr Ser Asn Leu Leu Ile Gly Met Glu
            180                 185                 190

Gly Asn Val Thr Pro Ala His Tyr Asp Glu Gln Gln Asn Phe Phe Ala
        195                 200                 205

Gln Ile Lys Gly Tyr Lys Arg Cys Ile Leu Phe Pro Pro Asp Gln Phe
    210                 215                 220

Glu Cys Leu Tyr Pro Tyr Pro Val His His Pro Cys Asp Arg Gln Ser
225                 230                 235                 240

Gln Val Asp Phe Asp Asn Pro Asp Tyr Glu Arg Phe Pro Asn Phe Gln
            245                 250                 255

Asn Val Val Gly Tyr Glu Thr Val Val Gly Pro Gly Asp Val Leu Tyr
            260                 265                 270

Ile Pro Met Tyr Trp Trp His His Ile Glu Ser Leu Leu Asn Gly Gly
        275                 280                 285

Ile Thr Ile Thr Val Asn Phe Trp Tyr Lys Gly Ala Pro Thr Pro Lys
    290                 295                 300

Arg Ile Glu Tyr Pro Leu Lys Ala His Gln Lys Val Ala Ile Met Arg
305                 310                 315                 320

Asn Ile Glu Lys Met Leu Gly Glu Ala Leu Gly Asn Pro Gln Glu Val
            325                 330                 335

Gly Pro Leu Leu Asn Thr Met Ile Lys Gly Arg Tyr Asn
            340                 345

<210> SEQ ID NO 3
<211> LENGTH: 352
<212> TYPE: PRT
<213> ORGANISM: Homo sapiens

<400> SEQUENCE: 3

Gly Ser His Met Ala Ala Thr Ala Ala Glu Ala Val Ala Ser Gly Ser
1               5                   10                  15

Gly Glu Pro Arg Glu Glu Ala Gly Ala Leu Gly Pro Ala Trp Asp Glu
            20                  25                  30
```

-continued

```
Ser Gln Leu Arg Ser Tyr Ser Phe Pro Thr Arg Pro Ile Pro Arg Leu
        35                  40                  45

Ser Gln Ser Asp Pro Arg Ala Glu Glu Leu Ile Glu Asn Glu Glu Pro
 50                  55                  60

Val Val Leu Thr Asp Thr Asn Leu Val Tyr Pro Ala Leu Lys Trp Asp
 65                  70                  75                  80

Leu Glu Tyr Leu Gln Glu Asn Ile Gly Asn Gly Asp Phe Ser Val Tyr
                     85                  90                  95

Ser Ala Ser Thr His Lys Phe Leu Tyr Tyr Asp Glu Lys Lys Met Ala
                100                 105                 110

Asn Phe Gln Asn Phe Lys Pro Arg Ser Asn Arg Glu Glu Met Lys Phe
            115                 120                 125

His Glu Phe Val Glu Lys Leu Gln Asp Ile Gln Gln Arg Gly Gly Glu
        130                 135                 140

Glu Arg Leu Tyr Leu Gln Gln Thr Leu Asn Asp Thr Val Gly Arg Lys
145                 150                 155                 160

Ile Val Met Asp Phe Leu Gly Phe Asn Trp Asn Trp Ile Asn Lys Gln
                165                 170                 175

Gln Gly Lys Arg Gly Trp Gly Gln Leu Thr Ser Asn Leu Leu Leu Ile
            180                 185                 190

Gly Met Glu Gly Asn Val Thr Pro Ala His Tyr Asp Glu Gln Gln Asn
        195                 200                 205

Phe Phe Ala Gln Ile Lys Gly Tyr Lys Arg Cys Ile Leu Phe Pro Pro
    210                 215                 220

Asp Gln Phe Glu Cys Leu Tyr Pro Tyr Pro Val His His Pro Cys Asp
225                 230                 235                 240

Arg Gln Ser Gln Val Asp Phe Asp Asn Pro Asp Tyr Glu Arg Phe Pro
                245                 250                 255

Asn Phe Gln Asn Val Val Gly Tyr Glu Thr Val Val Gly Pro Gly Asp
            260                 265                 270

Val Leu Tyr Ile Pro Met Tyr Trp Trp His His Ile Glu Ser Leu Leu
        275                 280                 285

Asn Gly Gly Ile Thr Ile Thr Val Asn Phe Trp Tyr Lys Gly Ala Pro
    290                 295                 300

Thr Pro Lys Arg Ile Glu Tyr Pro Leu Lys Ala His Gln Lys Val Ala
305                 310                 315                 320

Ile Met Arg Asn Ile Glu Lys Met Leu Gly Glu Ala Leu Gly Asn Pro
                325                 330                 335

Gln Glu Val Gly Pro Leu Leu Asn Thr Met Ile Lys Gly Arg Tyr Asn
            340                 345                 350
```

<210> SEQ ID NO 4
<211> LENGTH: 29
<212> TYPE: DNA
<213> ORGANISM: Artificial sequence
<220> FEATURE:
<223> OTHER INFORMATION: Primer

<400> SEQUENCE: 4
gggaattcca tatggcggcg acagcggcg                                   29

<210> SEQ ID NO 5
<211> LENGTH: 25
<212> TYPE: DNA
<213> ORGANISM: Artificial sequence
<220> FEATURE:

<223> OTHER INFORMATION: Primer

<400> SEQUENCE: 5
cgcggatccc tagttgtatc ggccc                                          25

<210> SEQ ID NO 6
<211> LENGTH: 35
<212> TYPE: DNA
<213> ORGANISM: Artificial sequence
<220> FEATURE:
<223> OTHER INFORMATION: Primer

<400> SEQUENCE: 6
gttatgattg tgaagttgct gctcctatac aaggc                               35

<210> SEQ ID NO 7
<211> LENGTH: 33
<212> TYPE: DNA
<213> ORGANISM: Artificial sequence
<220> FEATURE:
<223> OTHER INFORMATION: Primer

<400> SEQUENCE: 7
gtataggagc agcaacttca caatcataac tgg                                 33

<210> SEQ ID NO 8
<211> LENGTH: 35
<212> TYPE: DNA
<213> ORGANISM: Artificial sequence
<220> FEATURE:
<223> OTHER INFORMATION: Primer

<400> SEQUENCE: 8
gttatgattg tgaagttcaa gctcctatac aaggc                               35

<210> SEQ ID NO 9
<211> LENGTH: 33
<212> TYPE: DNA
<213> ORGANISM: Artificial sequence
<220> FEATURE:
<223> OTHER INFORMATION: Primer

<400> SEQUENCE: 9
gtataggacg ttgaacttca caatcataac tgg                                 33

<210> SEQ ID NO 10
<211> LENGTH: 35
<212> TYPE: DNA
<213> ORGANISM: Artificial sequence
<220> FEATURE:
<223> OTHER INFORMATION: Primer

<400> SEQUENCE: 10
gttatgattg tgaagttgaa gctcctatac aaggc                               35

<210> SEQ ID NO 11
<211> LENGTH: 35
<212> TYPE: DNA
<213> ORGANISM: Artificial sequence
<220> FEATURE:
<223> OTHER INFORMATION: Primer

<400> SEQUENCE: 11
ttgtatagga gcttcaactt cacaatcata actgg                               35

```
<210> SEQ ID NO 12
<211> LENGTH: 35
<212> TYPE: DNA
<213> ORGANISM: Artificial sequence
<220> FEATURE:
<223> OTHER INFORMATION: Primer

<400> SEQUENCE: 12
gttatgattg tgaagttgat gctcctatac aaggc                          35

<210> SEQ ID NO 13
<211> LENGTH: 35
<212> TYPE: DNA
<213> ORGANISM: Artificial sequence
<220> FEATURE:
<223> OTHER INFORMATION: Primer

<400> SEQUENCE: 13
ttgtatagga gcatcaactt cacaatcata actgg                          35
```